United States Patent
Harata et al.

(10) Patent No.: US 12,102,460 B2
(45) Date of Patent: Oct. 1, 2024

(54) X-RAY DOSE MANAGEMENT SYSTEM AND X-RAY DOSE MANAGEMENT METHOD

(71) Applicant: The Yoshida Dental Mfg. Co., Ltd., Tokyo (JP)

(72) Inventors: Yasuo Harata, Tokyo (JP); Kenichi Hosoda, Tokyo (JP); Nobuo Takahashi, Tokyo (JP); Daigo Inagaki, Tokyo (JP)

(73) Assignee: THE YOSHIDA DENTAL MFG. CO., LTD., Tokyo (JP)

( * ) Notice: Subject to any disclaimer, the term of this patent is extended or adjusted under 35 U.S.C. 154(b) by 394 days.

(21) Appl. No.: 17/777,676

(22) PCT Filed: Oct. 28, 2020

(86) PCT No.: PCT/JP2020/040427
§ 371 (c)(1),
(2) Date: May 18, 2022

(87) PCT Pub. No.: WO2021/100425
PCT Pub. Date: May 27, 2021

(65) Prior Publication Data
US 2022/0401044 A1    Dec. 22, 2022

(30) Foreign Application Priority Data

Nov. 18, 2019   (JP) .................................. 2019-207602

(51) Int. Cl.
*A61B 6/10* (2006.01)
*A61B 6/51* (2024.01)
(52) U.S. Cl.
CPC . *A61B 6/10* (2013.01); *A61B 6/51* (2024.01)
(58) Field of Classification Search
CPC .................................... A61B 6/10; A61B 6/51
See application file for complete search history.

(56) References Cited

U.S. PATENT DOCUMENTS

| | | | | |
|---|---|---|---|---|
| 5,138,646 | A | * 8/1992 | Hubert | A61B 6/4283 378/182 |
| 2001/0055368 | A1 | * 12/2001 | Carroll | H04N 25/30 348/E5.037 |

(Continued)

FOREIGN PATENT DOCUMENTS

| | | |
|---|---|---|
| JP | 2004147907 A | 5/2004 |
| JP | 2005305137 A | 11/2005 |

(Continued)

OTHER PUBLICATIONS

International Search Report and Written Opinion pertaining to PCT/JP2020/040427, mailed Dec. 22, 2020.

*Primary Examiner* — Blake C Riddick
(74) *Attorney, Agent, or Firm* — GRUMBLES LAW PLLC; Brittany Haanan

(57) ABSTRACT

In an X-ray dose management system, a dental radiograph device includes an imaging condition setter, an output information creator, and an information communicator that sends the output information to a wireless tag. An X-ray imaging element includes an X-ray image information obtainer and a wireless tag. An information reading device includes an output information reader and an information communicator that sends the read output information to an information terminal. The information terminal includes a patient information retriever that retrieves patient information from a patient information storage, a communicator that receives the output information, and an output information processor that records the output information and the patient information in association with each other in the patient information storage.

14 Claims, 19 Drawing Sheets

(56) References Cited

U.S. PATENT DOCUMENTS

| | | | |
|---|---|---|---|
| 2004/0086077 A1 | 5/2004 | Moriyama | |
| 2004/0086163 A1* | 5/2004 | Moriyama | A61B 6/00 705/2 |
| 2004/0184643 A1* | 9/2004 | Stantchev | G16H 40/63 382/128 |
| 2005/0213702 A1 | 9/2005 | Akagi | |
| 2005/0254625 A1* | 11/2005 | Schick | A61B 6/4233 378/91 |
| 2007/0103270 A1* | 5/2007 | Gmeinder | G06F 3/033 600/407 |
| 2007/0208999 A1* | 9/2007 | Gmeinder | G06F 3/14 715/700 |
| 2009/0022276 A1* | 1/2009 | Ohara | A61B 6/4283 378/101 |
| 2009/0162808 A1* | 6/2009 | Nyholm | A61C 1/0015 433/25 |
| 2010/0185459 A1* | 7/2010 | Vera | A61B 6/5294 705/3 |
| 2013/0188629 A1* | 7/2013 | Lemaire | H04W 4/80 370/338 |
| 2014/0010350 A1* | 1/2014 | De Godzinsky | A61B 6/06 378/62 |
| 2014/0049380 A1* | 2/2014 | Berger | A61B 6/4494 340/10.52 |
| 2014/0088997 A1* | 3/2014 | Arefieg | G06Q 10/087 705/2 |
| 2014/0161235 A1* | 6/2014 | Taskinen | A61B 6/463 378/189 |
| 2014/0191852 A1* | 7/2014 | Inglese | A61B 6/4411 340/10.52 |
| 2014/0304638 A1* | 10/2014 | Yoshikawa | A61B 6/563 715/771 |
| 2015/0036800 A1* | 2/2015 | Takemoto | A61B 6/032 378/62 |
| 2015/0063542 A1* | 3/2015 | Park | A61B 6/542 378/62 |
| 2015/0238162 A1* | 8/2015 | Berger | A61B 6/4494 378/62 |
| 2015/0294066 A1* | 10/2015 | Golay | A61B 6/51 433/29 |
| 2015/0324680 A1* | 11/2015 | Berger | A61B 6/4216 235/375 |
| 2016/0012182 A1* | 1/2016 | Golay | G16H 40/20 705/3 |
| 2016/0374638 A1 | 12/2016 | Kubota | |
| 2017/0079602 A1* | 3/2017 | Lim | G03B 42/042 |
| 2017/0215997 A1* | 8/2017 | Martin | A61B 90/50 |
| 2017/0319160 A1* | 11/2017 | Lu | A61B 6/512 |
| 2018/0039733 A1* | 2/2018 | Golay | G16H 30/20 |
| 2018/0184990 A1* | 7/2018 | Shin | H05G 1/12 |
| 2019/0150876 A1* | 5/2019 | Kagermeier | A61B 6/548 |
| 2019/0328466 A1* | 10/2019 | Schwägli | G06T 7/73 |

FOREIGN PATENT DOCUMENTS

| | | |
|---|---|---|
| JP | 2012217572 A | 11/2012 |
| JP | 2015112391 A | 6/2015 |
| JP | 2015177964 A | 10/2015 |
| JP | 2015195811 A | 11/2015 |
| WO | 2016208229 A1 | 12/2016 |

* cited by examiner

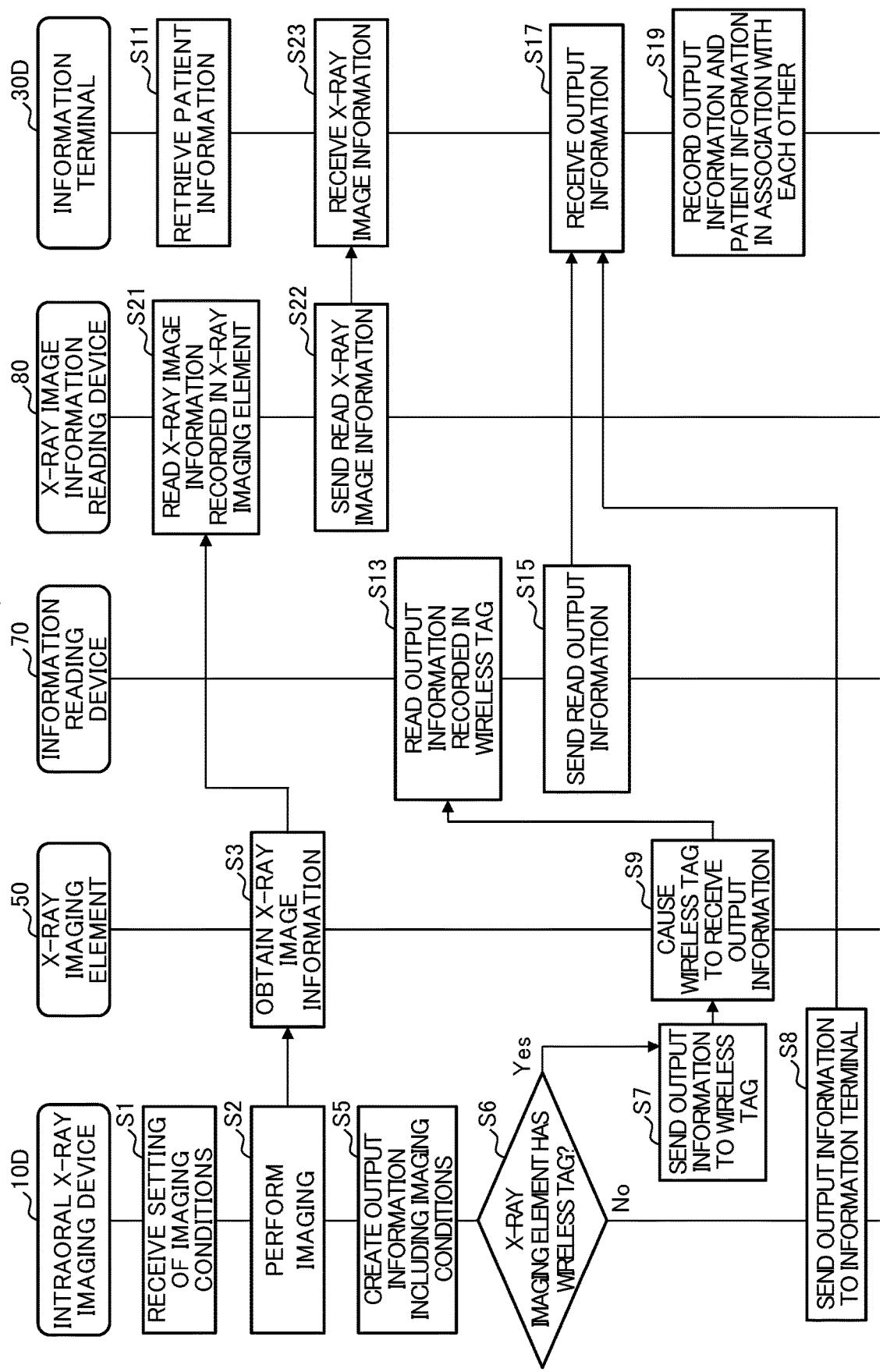

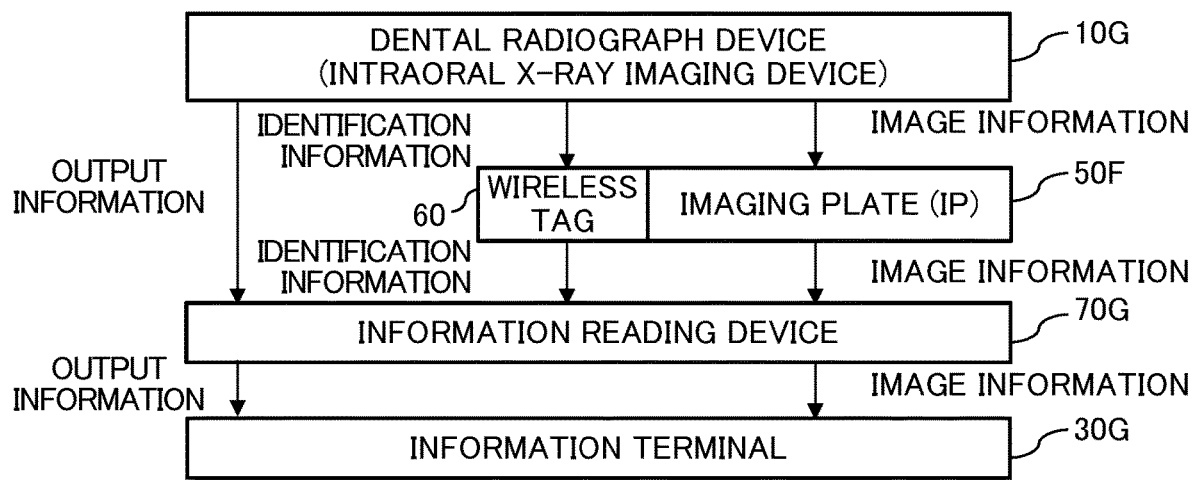
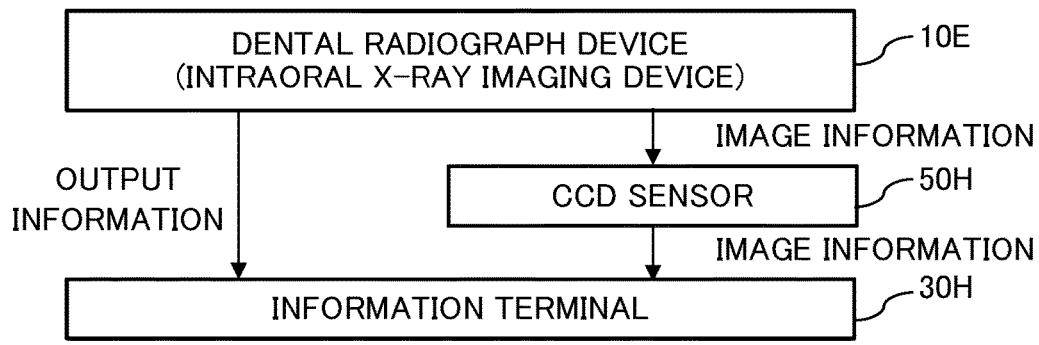

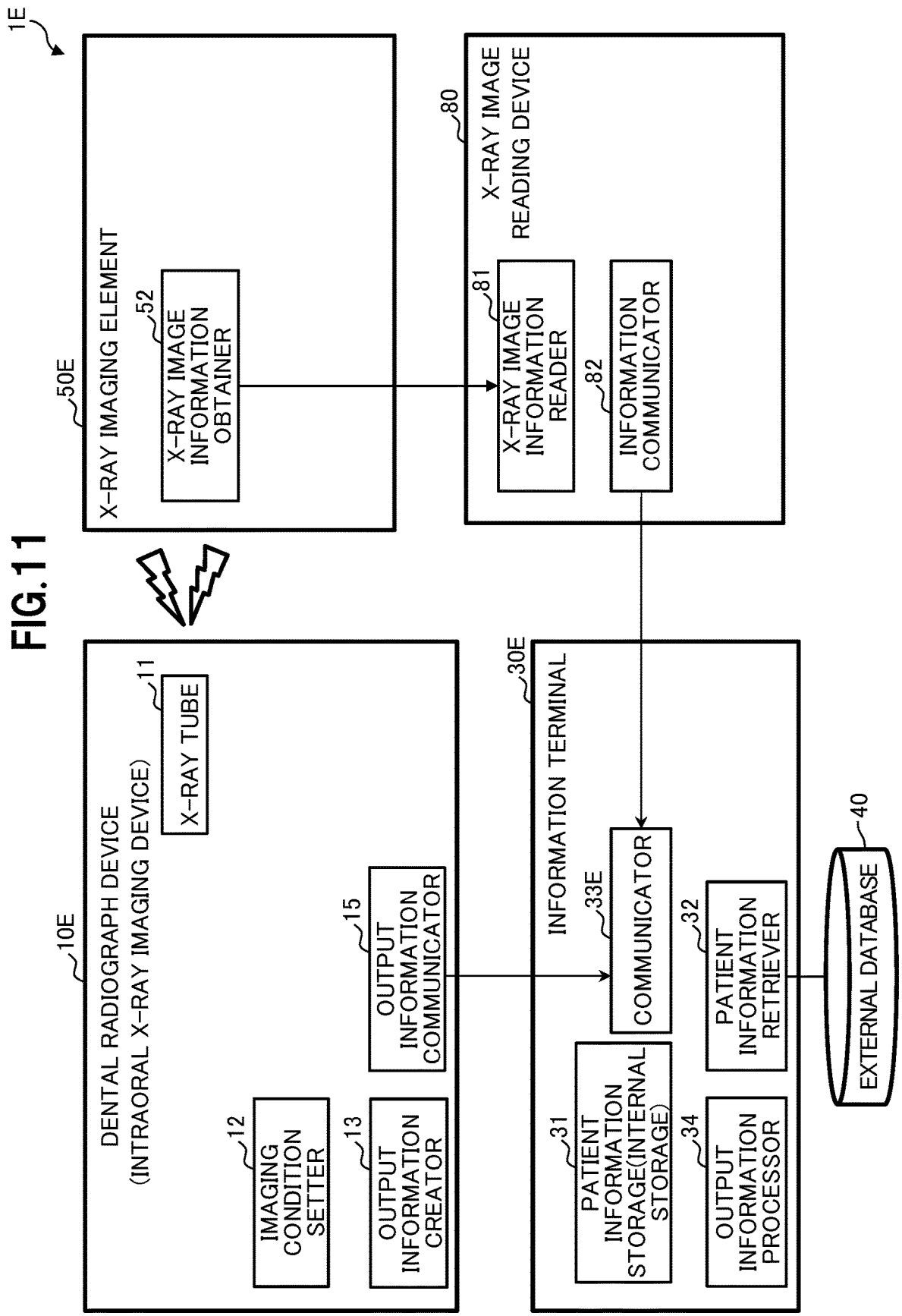

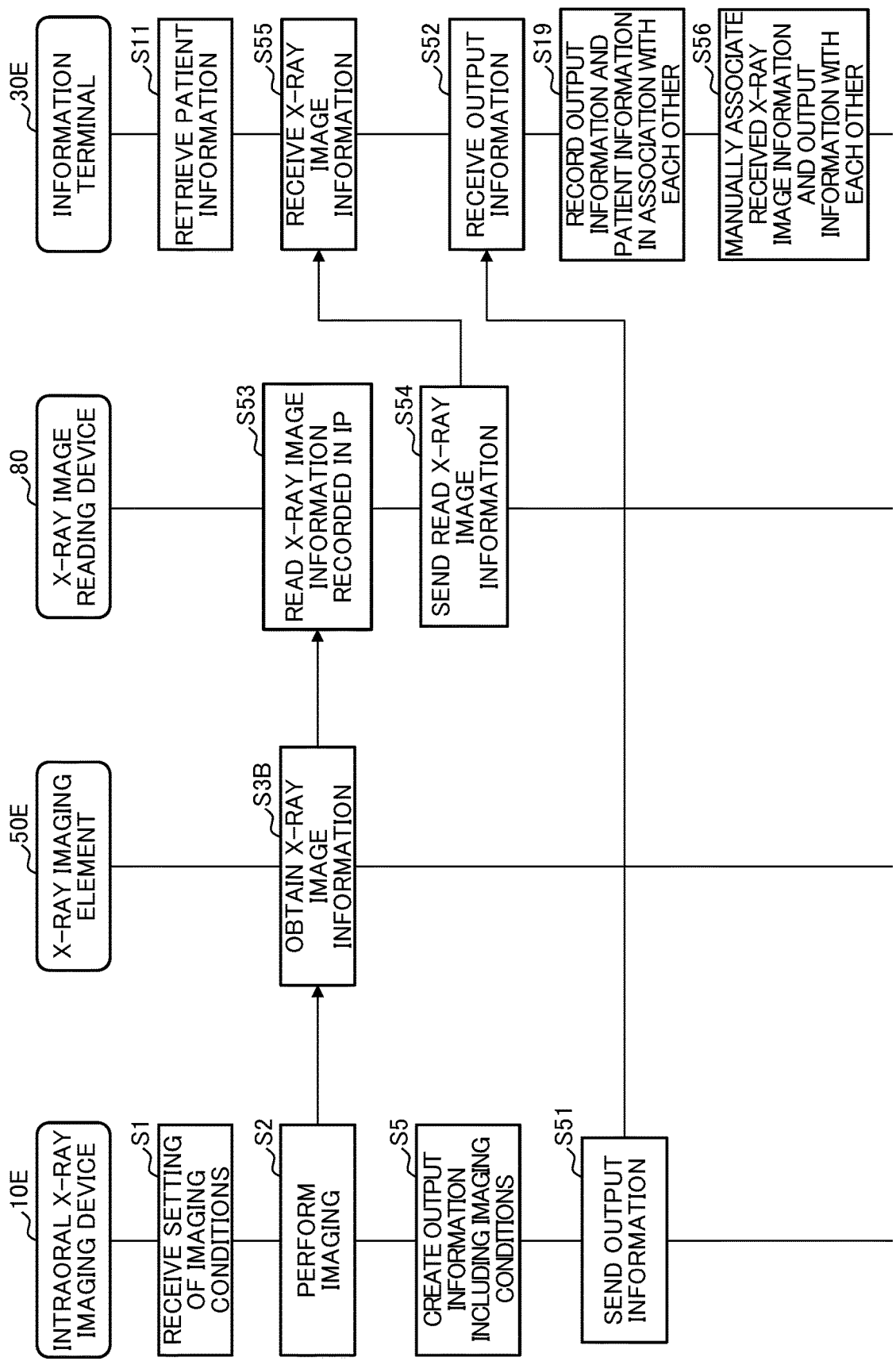

X-RAY DOSE MANAGEMENT SYSTEM AND X-RAY DOSE MANAGEMENT METHOD

TECHNICAL FIELD

The present invention relates to an X-ray dose management system and an X-ray dose management method.

BACKGROUND ART

A dental X-ray panorama imaging device has been conventionally known (see Patent Literature 1). In conventional digital panorama imaging and CT imaging, in each imaging operation, patient information is retrieved in an information terminal, imaging conditions and the like are determined on the information terminal, and then a patient is introduced to perform the imaging. Accordingly, X-ray image information and the patient information can be easily associated with the imaging conditions and dose management can be easily performed.

CITATION LIST

Patent Literature

Patent Literature 1: JP2015-177964A

SUMMARY OF INVENTION

Technical Problem

However, in intraoral X-ray imaging in which an X-ray imaging element is arranged in the oral cavity of a patient, imaging is performed by setting the imaging conditions on the intraoral X-ray imaging device side and obtaining the X-ray image information with the X-ray imaging element. After the imaging, an information terminal separate from the intraoral X-ray imaging device obtains X-ray image information recorded in the X-ray imaging element. This X-ray image information does not include the imaging conditions and the like. Accordingly, the X-ray image information, the patient information, the imaging conditions, and the like are not associated with one another. If the association is necessary, a dentist or the like has to input the imaging conditions and the like into the patient information by himself/herself.

The present invention has been made in view of the aforementioned circumstances and an object is to provide an X-ray dose management system and an X-ray dose management method that manage exposed dose of each patient in intraoral X-ray imaging.

Solution to Problem

To solve the above-described problem, an X-ray dose management system according to the present invention includes: an intraoral X-ray imaging device; an X-ray imaging element; an information reading device; and an information terminal, in which the intraoral X-ray imaging device includes: an imaging condition setter that is used to set an imaging condition for performing intraoral X-ray imaging; an output information creator that creates output information including identification information of imaging time and date, dose information, and the imaging condition; and an information communicator that sends the output information to an external device by wireless communication, the X-ray imaging element includes: an X-ray image information obtainer that obtains X-ray image information acquired by X-ray imaging; and a wireless tag that receives the output information from the intraoral X-ray imaging device, the information reading device includes: an output information reader that reads the output information recorded in the wireless tag; and an information communicator that sends the read output information to the information terminal, and the information terminal includes: a patient information retriever that retrieves patient information on a patient subjected to X-ray imaging from an internal storage or an external database in which the patient information is stored; a communicator that receives the output information; and an output information processor that records the received output information and the patient information retrieved by the patient information retriever in association with each other in the internal storage or the external database.

Advantageous Effects of Invention

The present invention can manage exposed dose of each patient in intraoral X-ray imaging.

BRIEF DESCRIPTION OF DRAWINGS

FIG. 9 is a sequence diagram schematically showing a flow of a process in the X-ray dose management system according to the fourth embodiment of the present invention.

FIG. 10C is a block diagram schematically showing a flow of information in an X-ray dose management system according to a seventh embodiment of the present invention.

FIG. 10D is a block diagram schematically showing a flow of information in an X-ray dose management system according to an eighth embodiment of the present invention.

FIG. 11 is a block diagram schematically showing a configuration of the X-ray dose management system according to the fifth embodiment of the present invention.

FIG. 12 is a sequence diagram schematically showing a flow of a process in the X-ray dose management system according to the fifth embodiment of the present invention.

DESCRIPTION OF EMBODIMENTS

First Embodiment

[Configuration of X-Ray Dose Management System]

Figure 1:
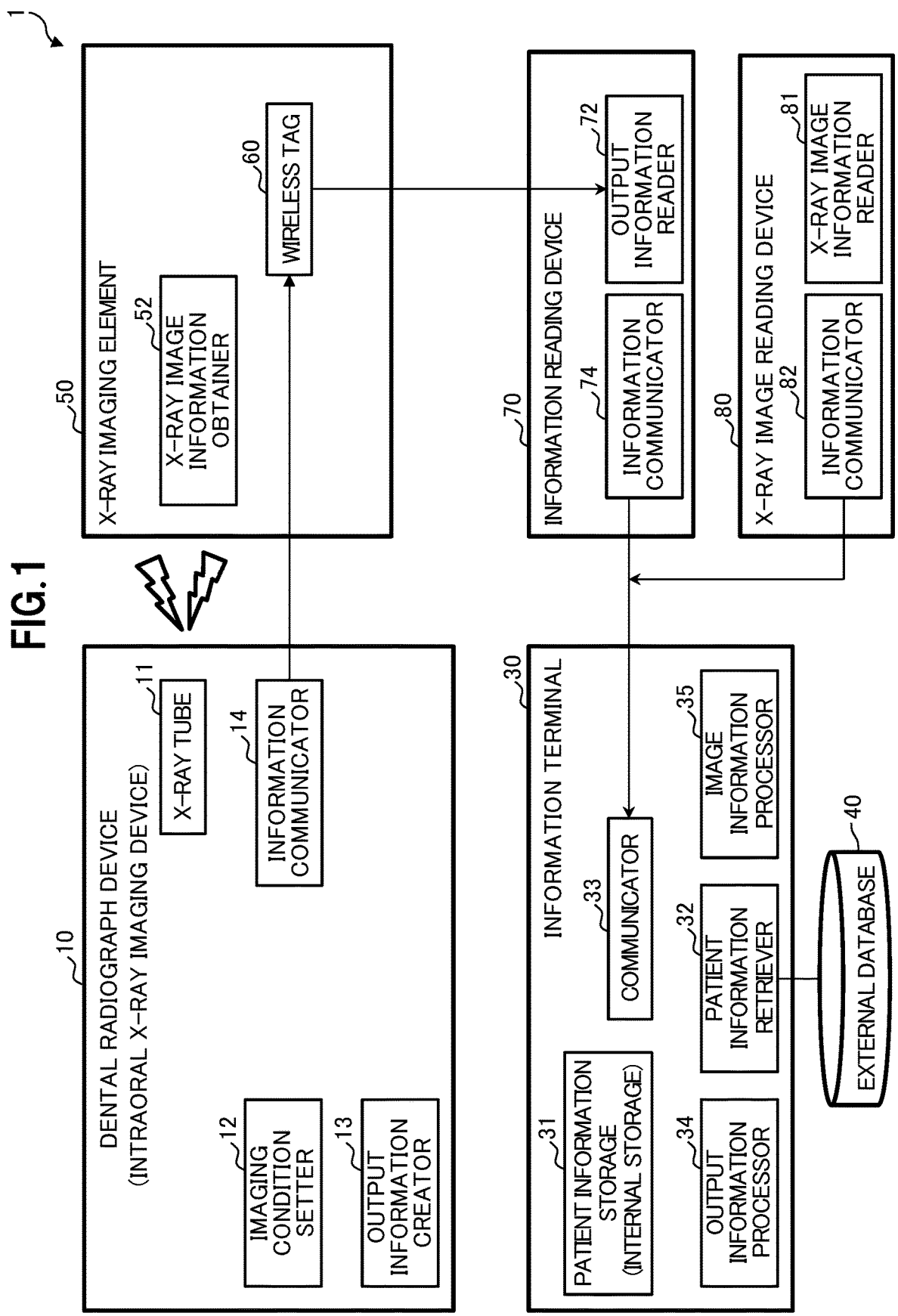
FIG. 1 is a block diagram schematically showing a configuration of an X-ray dose management system according to a first embodiment of the present invention.

As shown in FIG. 1, an X-ray dose management system 1 includes an intraoral X-ray imaging device 10 (hereinafter, also referred to as dental radiograph device 10), an X-ray imaging element 50, an information reading device 70, and an information terminal 30.

The intraoral X-ray imaging device 10 includes an X-ray tube 11, an imaging condition setter 12 that is a controller, an output information creator 13, and an information communicator 14. The X-ray tube 11 is a general configuration member used for X-ray imaging. The imaging condition setter 12 receives setting of imaging conditions for performing intraoral X-ray imaging. The imaging conditions include, for example, output voltage (kV), output current (mA), imaging time (sec), and the like.

The output information creator 13 creates output information including identification information of imaging time and date, dose information, and the imaging conditions. The output information creator 13 creates the output information in which predetermined necessary matters are written in a predetermined format such as a table format. In this case, the imaging time and date includes, for example, hour, minute, and second of the imaging date. Moreover, the dose information includes an amount (Sievert) of radiation in dental X-ray imaging in dental therapy. Note that a method of imaging with 10 standard films (10-film method), a method of imaging with 14 standard films (14-film method), and the like are known. For example, in the 10-film method, the amount of radiation for 10 dental X-ray images may be set as the dose information. The output information may also include imaged portion information relating to imaged portions. For example, information on positions specified in advance in a standard imaging method such as the 10-film method can be used as the imaged portion information.

The information communicator 14 sends the output information to a wireless tag 60 that is an external device by wireless communication. The information communicator 14 writes the output information in the wireless tag 60.

The wireless tag 60 is a contactless tag, for example, a RF tag, a microchip, or the like that uses RFID (radio frequency identification). Description is given below assuming that the wireless tag 60 is a tag that uses RFID as an example. In this case, the information communicator 14 includes a RFID reader-writer.

A general X-ray imaging element used for X-ray imaging in a general intraoral X-ray imaging device can be used as the X-ray imaging element 50. The X-ray imaging element 50 is, for example, an X-ray film, an imaging plate (hereinafter, referred to as IP), a CCD (charge coupled device) sensor, a CMOS (complementary MOS) sensor, or the like.

The X-ray imaging element 50 includes an X-ray image information obtainer 52 and the wireless tag 60. The X-ray image information obtainer 52 is a member that obtains X-ray image information acquired by X-ray imaging. The wireless tag 60 is attached at a predetermined position of the X-ray imaging element 50 such as a back surface where it does not affect the X-ray imaging, and receives the output information from the intraoral X-ray imaging device 10.

The information reading device 70 is a device that reads the output information from the wireless tag 60. The information reading device 70 includes an output information reader 72 and an information communicator 74. The output information reader 72 is a unit that reads the output information recorded in the wireless tag 60. When the wireless tag 60 is a tag that uses RFID, the output information reader 72 includes a RFID reader-writer. The information communicator 74 is a unit that sends the output information read by the output information reader 72 to the information terminal 30. Communication between the information communicator 74 and the information terminal 30 may be wired or wireless communication.

The information terminal 30 includes a patient information storage (internal storage) 31, a patient information retriever 32, a communicator 33, and an output information processor 34. The information terminal 30 can be formed of, for example, a personal computer (PC), a tablet PC, or a smartphone.

The patient information storage (internal storage) 31 stores patient information and is formed of, for example, a general memory and the like. The patient information is general information on a patient subjected to X-ray imaging and includes, for example, personal information identifying the patient, therapy information, dose information, and the like. The dose information includes, for example, information on accumulated dose over the last one year.

Note that the patient information may be stored in an external database 40 outside the information terminal 30, instead of the internal storage. The external database 40 may be a database built in a network device such as a receipt computer or a PC in a dental clinic or a database built in a network device such as cloud.

The patient information retriever 32 is a unit that manually or automatically retrieves the patient information from the patient information storage 31 or the external database 40 in which the patient information is stored. When the patient information is to be manually retrieved, for example, an operator operates the information terminal 30 and causes the patient information retriever 32 to read the patient information on the patient subjected to X-ray imaging and display the patient information on a screen display unit of the information terminal 30. Alternatively, the patient information may be automatically retrieved from the external database 40 in which the patient information is stored and displayed without intentional retrieval by the operator by using occurrence a predetermined event as a trigger. For example, coming of predetermined time such as appointment time of the patient may be used as a trigger. Moreover, execution of a predetermined operation such as an operation of reading information from a registration card of the patient at reception may be used as a trigger. Moreover, the intraoral X-ray imaging device 10 may be provided with a camera that captures an image of the patient's face. When an image of the face of the patient is captured with this camera and the patient is identified by facial recognition performed on the captured image, this identification may be used as a trigger. Description is given below assuming that the operator operates the information terminal 30 to cause the patient information retriever 32 to display the patient information on the screen display unit of the information terminal 30 as an example.

The communicator 33 is a general communication function of the information terminal 30 that is communication with an information communication network. The communicator 33 receives the output information from the information reading device 70 by wireless or wired communication. The output information processor 34 records the received output information and the patient information retrieved by the patient information retriever 32 in association with each other in the patient information storage 31 or the external database 40.

The information terminal 30 may include an image information processor 35 that performs control of reading the X-ray image information in the information terminal 30 and displaying it on an image display unit of the information terminal 30 and control of recording the X-ray image information. When the output information includes the imaged portion information on the imaged portions as described above, the image information processor 35 arranges and displays captured images at predetermined positions based on the imaged portion information. When the output information includes no imaged portion information, the information terminal 30 may assume the imaged portions by performing image processing on the captured images and arrange the captured images at predetermined positions based on the assumed imaged portions.

The X-ray dose management system 1 includes an X-ray image reading device 80 when the X-ray imaging element 50 is, for example, the IP. The X-ray image reading device 80 includes an X-ray image information reader 81 and an information communicator 82. The X-ray image information reader 81 is a unit that reads (scans) the X-ray image information from the IP. The information communicator 82 is a unit that sends the X-ray image information read from the IP to an external device. The information communicator 82 sends the X-ray image information to, for example, the information terminal 30. The X-ray image reading device 80 can be formed of a so-called IP scanner.

[Operation of X-Ray Dose Management System]

Figure 2:
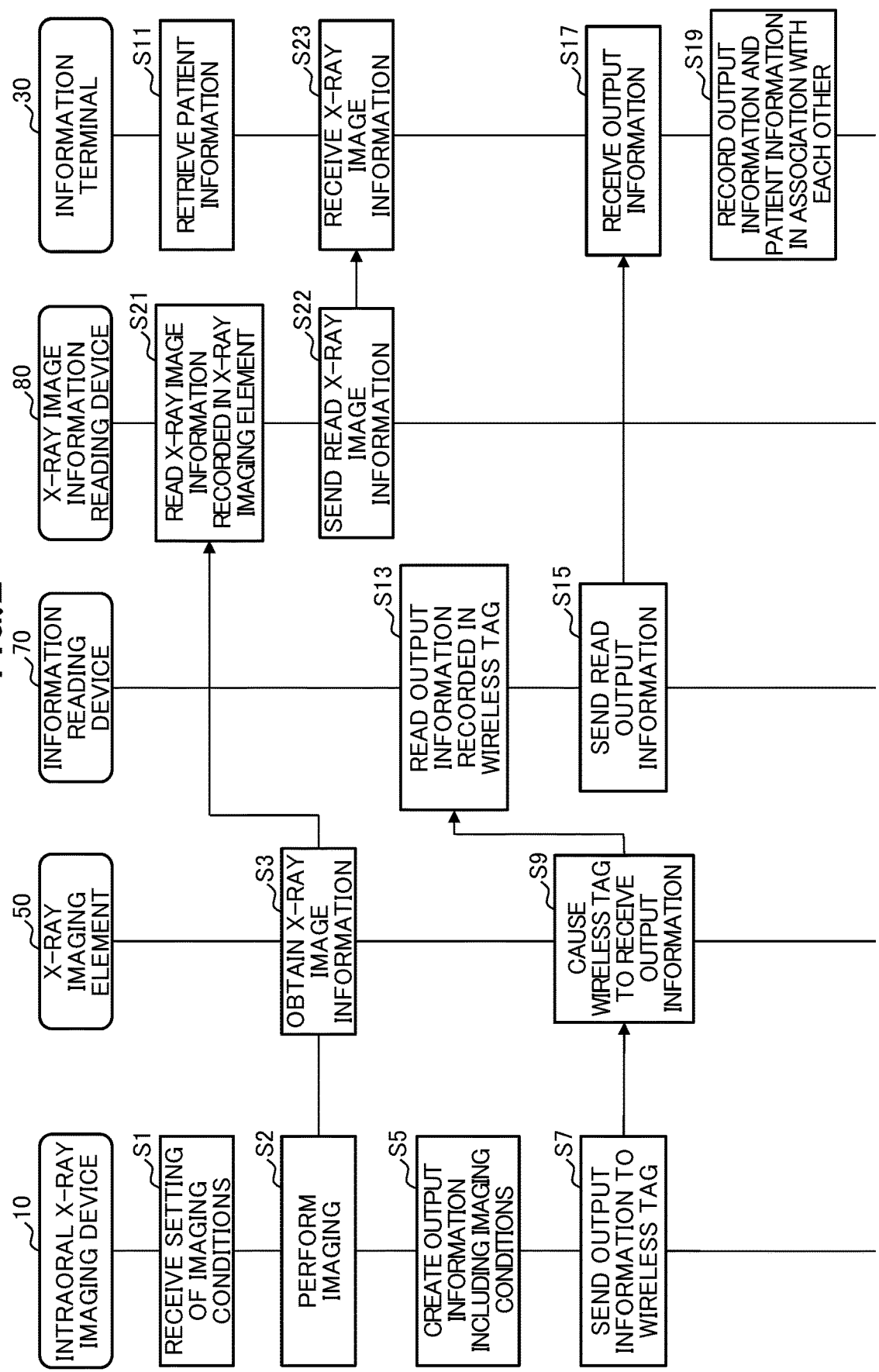
FIG. 2 is a sequence diagram schematically showing a flow of a process in the X-ray dose management system according to the first embodiment of the present invention.

Next, an operation of the X-ray dose management system 1 is described with reference to FIG. 2 (with reference to FIG. 1 as appropriate). In the intraoral X-ray imaging device 10, the imaging condition setter 12 receives the setting of the imaging conditions (step S1). Then, the intraoral X-ray imaging device 10 performs imaging with the X-ray imaging element 50 inserted in the oral cavity of the patient (step S2). The X-ray imaging element 50 thereby obtains the X-ray image information (step S3). Then, the X-ray imaging element 50 is taken out from the oral cavity of the patient.

Next, the intraoral X-ray imaging device 10 creates the output information including the identification information of the imaging time and date, the dose information, and the imaging conditions (step S5). Then, the intraoral X-ray imaging device 10 sends the output information from the information communicator 14 to the wireless tag 60 provided in the X-ray imaging element 50 (step S7). The wireless tag 60 receives the output information from the intraoral X-ray imaging device 10 (step S9).

Meanwhile, the operator operates the information terminal 30 to retrieve the patient information on the patient subjected to X-ray imaging from the patient information storage 31 or the external database 40 in which the patient information is stored, in the information terminal 30 (step S11). Moreover, the operator brings the X-ray imaging element 50 with the wireless tag 60 close to the information reading device 70. The information reading device 70 reads the output information recorded in the wireless tag 60 (step S13). Then, the information reading device 70 sends the read output information to the information terminal 30 (step S15). The information terminal 30 receives the output information from the information reading device 70 (step S17). Then, the information terminal 30 records the received output information and the patient information retrieved by the patient information retriever 32 in association with each other in the patient information storage 31 or the external database 40 (step S19).

Figure 3A:
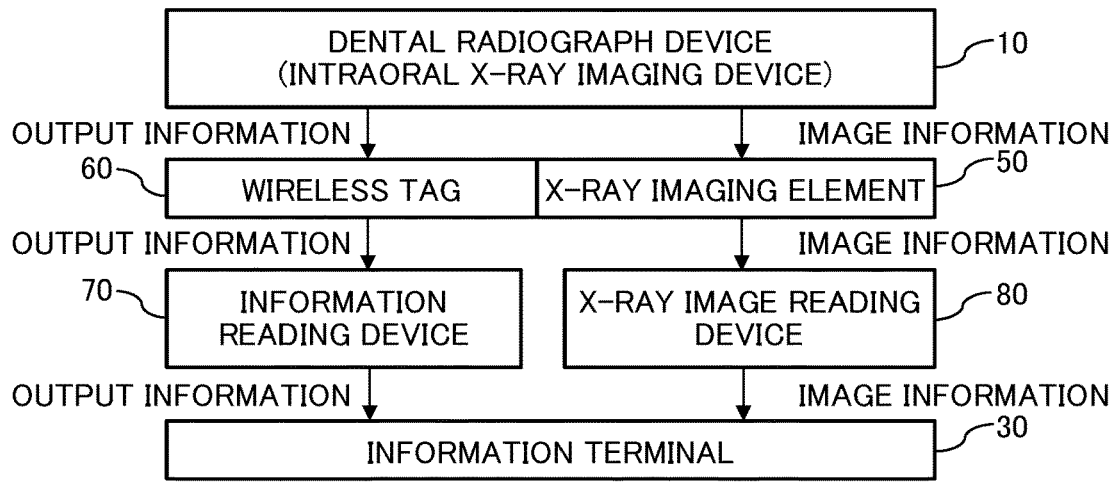
FIG. 3A is a block diagram schematically showing a flow of information in the X-ray dose management system according to the first embodiment of the present invention.

As shown in a left portion of FIG. 3A, the aforementioned output information is transmitted in the order of the dental radiograph device (intraoral X-ray imaging device) 10 to the wireless tag 60, to the information reading device 70, and to the information terminal 30. Meanwhile, as shown in a right portion of FIG. 3A, the image information is transmitted in the order of the dental radiograph device (intraoral X-ray imaging device) 10 to the X-ray imaging element 50, to the X-ray image reading device 80, and to the information terminal 30 when the X-ray imaging element 50 is, for example, the IP. Specifically, as shown in FIG. 2, the X-ray image reading device 80 reads the X-ray image information recorded in the X-ray imaging element 50 (step S21). Then, the X-ray image reading device 80 sends the read X-ray image information to the information terminal 30 (step S22). The information terminal 30 thereby receives the X-ray image information (step S23). Note that the aforementioned process flow is an example, and the order of processes can be changed as appropriate. For example, the process of step S11 may be performed first.

The X-ray dose management system 1 can transmit the output information, created by determining the imaging conditions and the like and performing imaging on the intraoral X-ray imaging device 10, to the information terminal 30 via the wireless tag 60 and the information reading device 70. Accordingly, an exposed dose of each patient can be managed by associating the patient information retrieved in the information terminal 30 with the output information, that is the dose information, the imaging conditions, and the like in intraoral X-ray imaging.

Second Embodiment

Next, description is given of an embodiment in which the X-ray imaging element 50 is the IP and the information reading device 70 has the function of the IP scanner. Note that, in the following description of the embodiment, the same configurations as those in the first embodiment are denoted by the same reference numerals with description thereof omitted as appropriate and different functions and different configurations are described.

[Configuration of X-Ray Dose Management System]

Figure 4:
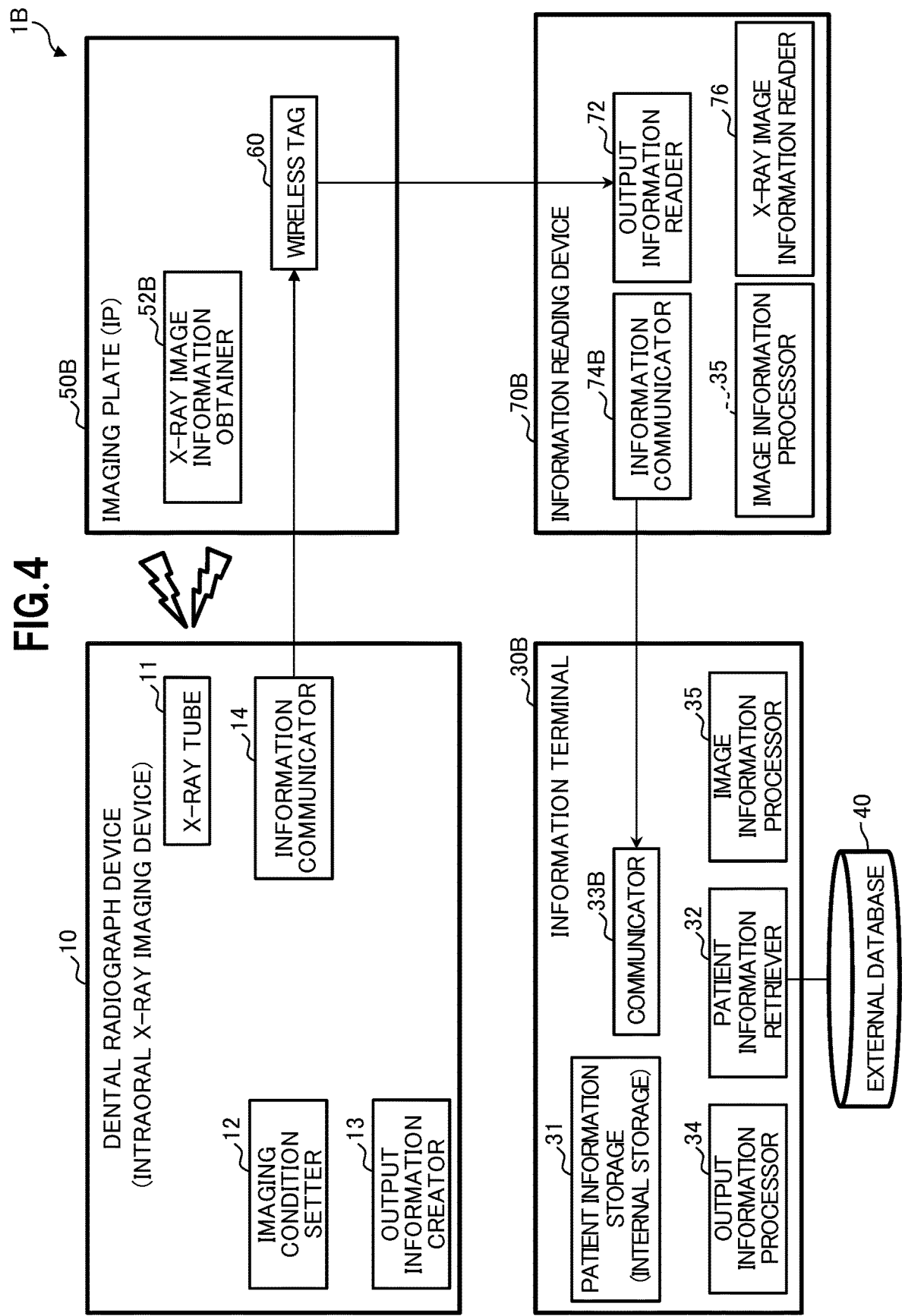
FIG. 4 is a block diagram schematically showing a configuration of the X-ray dose management system according to the second embodiment of the present invention.

As shown in FIG. 4, an X-ray dose management system 1B includes the intraoral X-ray imaging device 10, an IP 50B that is the X-ray imaging element, an information reading device 70B, and an information terminal 30B.

The IP 50B includes an X-ray image information obtainer 52B and the wireless tag 60. The X-ray image information obtainer 52B is made of a phosphor layer for image recording applied onto a substrate of the IP and obtains the X-ray image information acquired by X-ray imaging. The wireless tag 60 is attached to a back surface of the substrate of the IP that is on the opposite side to the side where the phosphor layer is arranged.

The information reading device 70B includes the output information reader 72, an information communicator 74B, and an X-ray image information reader 76. The X-ray image information reader 76 reads the X-ray image information recorded in the IP 50B. The information communicator 74B sends the read X-ray image information to the information terminal 30B. The X-ray image information reader 76 and the information communicator 74B can be formed of a so-called IP scanner. Specifically, the information reading device 70B can be formed by arranging the output information reader 72 formed of, for example, a RFID reader-writer in a predetermined portion of a publicly known IP scanner.

The information terminal 30B includes the patient information storage (internal storage) 31, the patient information retriever 32, a communicator 33B, the output information processor 34, and the image information processor 35. The communicator 33B receives the output information and the X-ray image information from the information reading device 70B.

The image information processor 35 associates the output information and the X-ray image information with each other. The image information processor 35 records the output information and the X-ray image information in association with each other in the patient information storage 31 or the external database 40. The X-ray image information, the patient information, and the output information including the dose information and the imaging conditions can be thereby associated with one another.

As a modified example, the information reading device 70B may include the image information processor 35 that associates the output information and the X-ray image information with each other. Moreover, at least one of the information reading device 70B and the information terminal 30B may include the image information processor 35 that associates the output information and the X-ray image information with each other.

[Operation of X-Ray Dose Management System]

Figure 5:
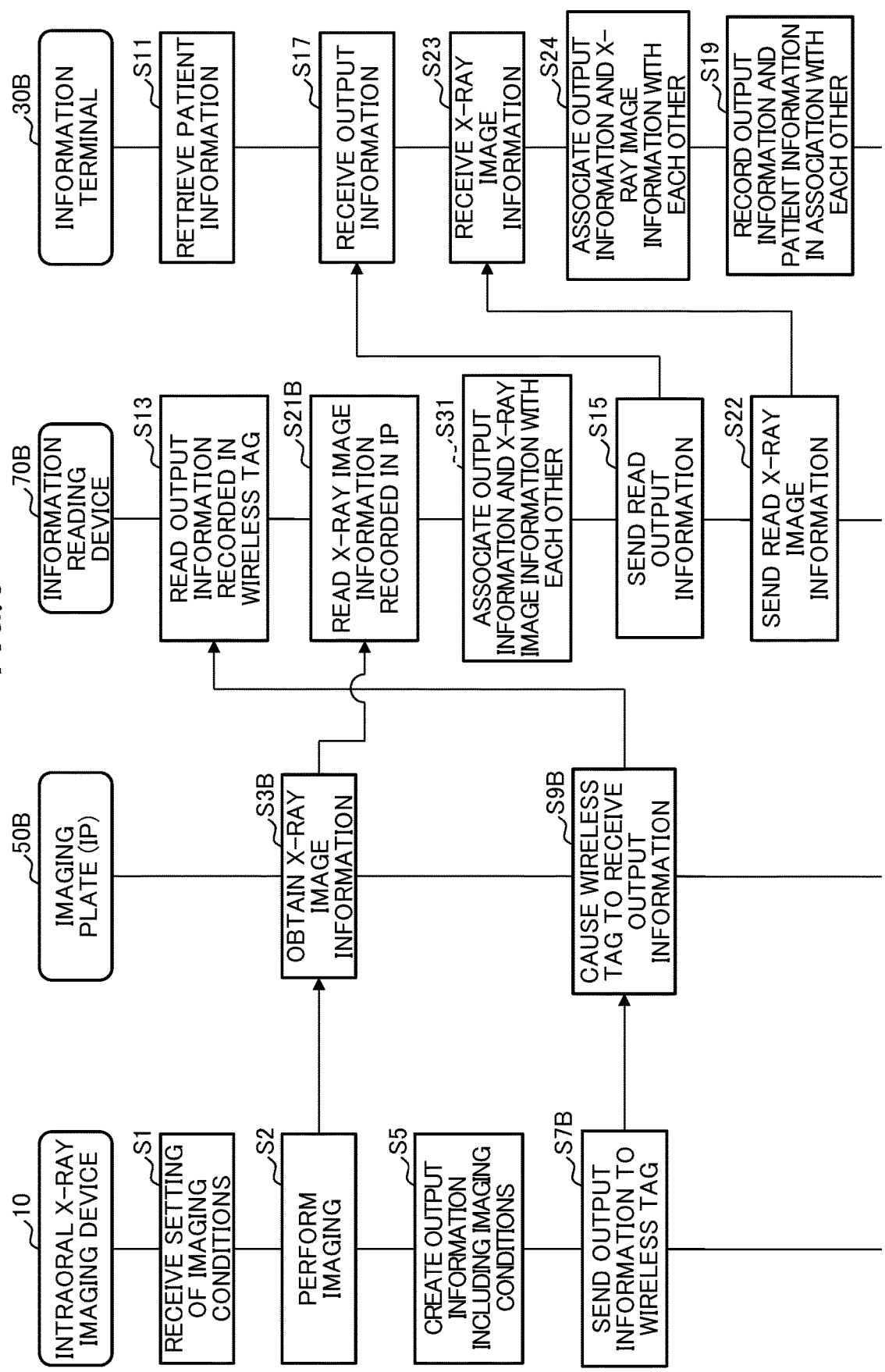
FIG. 5 is a sequence diagram schematically showing a flow of a process in the X-ray dose management system according to the second embodiment of the present invention.

Next, an operation of the X-ray dose management system 1B is described with reference to FIG. 5 (with reference to FIG. 4 as appropriate). Note that, in the following description, the same processes as those in the first embodiment are denoted by the same reference numerals with description thereof omitted as appropriate and different functions and different processes are described.

The intraoral X-ray imaging device 10 receives the setting of the imaging conditions (step S1) and performs imaging (step S2). The IP 50B obtains the X-ray image information (step S3B). Then, the intraoral X-ray imaging device 10 creates the output information (step S5) and sends the output information to the wireless tag 60 provided in the IP 50B (step S7B). The wireless tag 60 provided in the IP 50B receives the output information (step S9B).

Moreover, the operator inserts the IP 50B with the wireless tag 60 in the information reading device 70B. The information reading device 70B reads the output information recorded in the wireless tag 60 (step S13). Furthermore, the information reading device 70B reads the X-ray image information recorded in the IP 50B (step S21B). Then, the information reading device 70B sends the read output information to the information terminal 30B (step S15) and sends the read X-ray image information to the information terminal 30B (step S22). The information terminal 30B thereby receives the output information (step S17) and receives the X-ray image information (step S23) from the information reading device 70B. Then, in the information terminal 30B, the image information processor 35 associates the received output information and the received X-ray image information with each other (step S24). Moreover, the information terminal 30B records the received output information and the patient information retrieved in step S11 in association with each other in the patient information storage 31 or the external database 40 (step S19).

As a modified example, when the information reading device 70B includes the image information processor 35, the information reading device 70B may associate the read output information and the read X-ray image information with each other (step S31) and then send the output information and the X-ray image information to the information terminal 30B in step S15 and step S22. Note that step S13 and step S21B may be executed in the reverse order or simultaneously. Furthermore, step S15 and step 22 as well as step 17 and step S23 may be executed in reverse order or simultaneously.

Figure 3B:
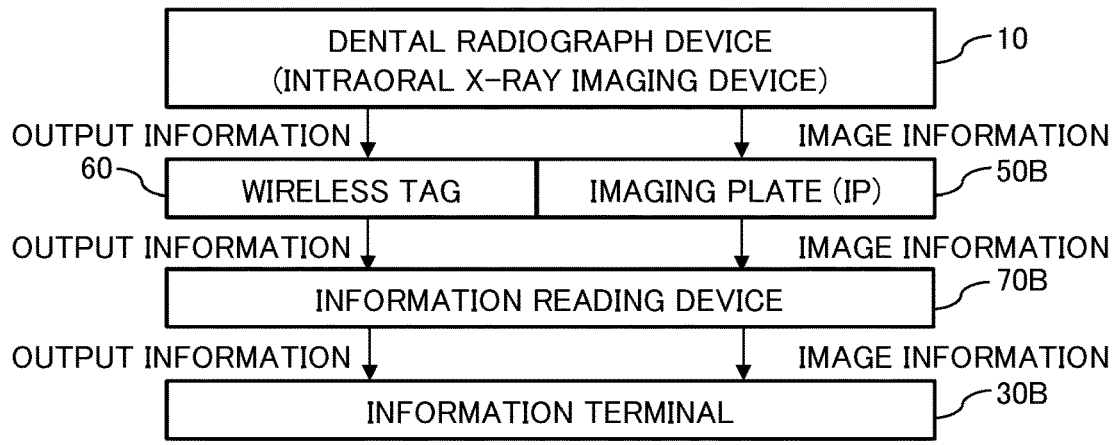
FIG. 3B is a block diagram schematically showing a flow of information in an X-ray dose management system according to a second embodiment of the present invention.

As shown in a left portion of FIG. 3B, the aforementioned output information is transmitted in the order of the dental radiograph device (intraoral X-ray imaging device) 10 to the wireless tag 60, to the information reading device 70B, and to the information terminal 30B. The X-ray dose management system 1B can thereby manage the exposed dose of each patient as in the first embodiment. Note that, as shown in a right portion of FIG. 3B, the image information is sent in the order of the dental radiograph device (intraoral X-ray imaging device) 10 to the IP 50B, to the information reading device 70B, and to the information terminal 30B.

Third Embodiment

Next, description is given of an embodiment in which the X-ray imaging element 50 is a CCD sensor. Note that, in the following description of the embodiment, the same configurations as those in the first embodiment are denoted by the same reference numerals with description thereof omitted as appropriate and different functions and different configurations are described.

[Configuration of X-Ray Dose Management System]

Figure 6:
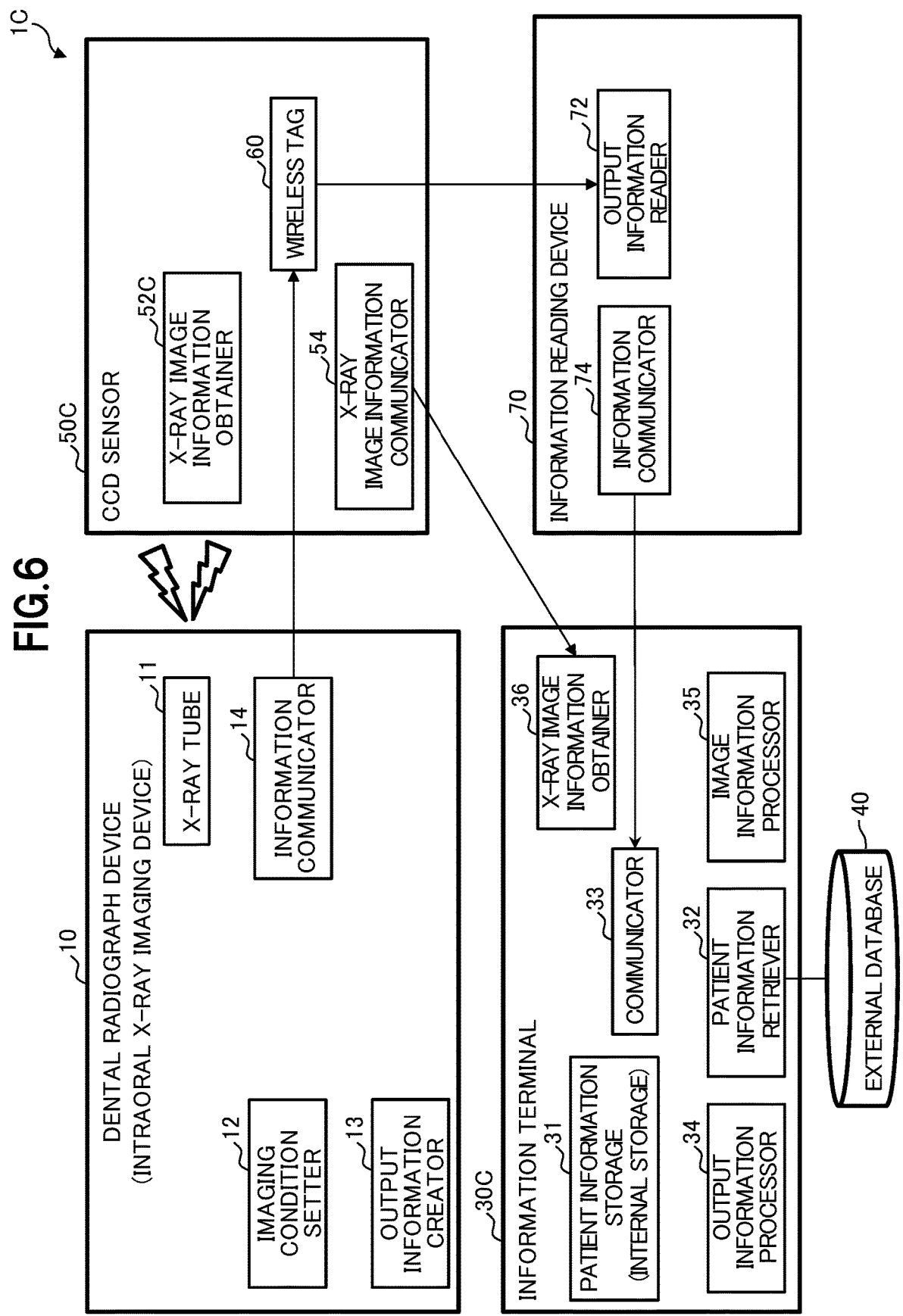
FIG. 6 is a block diagram schematically showing a configuration of the X-ray dose management system according to the third embodiment of the present invention.

As shown in FIG. 6, an X-ray dose management system 1C includes the intraoral X-ray imaging device 10, a CCD sensor 50C that is the X-ray imaging element, the information reading device 70, and an information terminal 30C.

The CCD sensor 50C includes an X-ray image information obtainer 52C, an X-ray image information communicator 54, and the wireless tag 60. The X-ray image information obtainer 52C includes a light receiving surface that forms an outer surface of a case of the CCD sensor, a scintillator (phosphor layer) that is arranged below the light receiving surface, an optical fiber bundle that guides light from the scintillator, and a CCD element that converts the light from the optical fiber bundle to an electric signal, and obtains the X-ray image information acquired by X-ray imaging. The wireless tag 60 is attached to a surface (back surface or side surface) of the case of the CCD sensor other than the light receiving surface. The X-ray image information communicator 54 is a unit that sends the X-ray image information to the information terminal 30C. The X-ray image information communicator 54 is formed of, for example, a communication cable that transmits the electric signal from the CCD element to the information terminal 30C. Note that communication of transmitting the X-ray image information to the information terminal 30C may be wired or wireless communication.

The information terminal 30C includes the patient information storage (internal storage) 31, the patient information retriever 32, the communicator 33, the output information processor 34, the image information processor 35, and an X-ray image information obtainer 36. The X-ray image information obtainer 36 is a unit that obtains the X-ray image information from the CCD sensor 50C. When the X-ray image information communicator 54 of the CCD sensor 50C is formed of a communication cable, the X-ray image information obtainer 36 is also formed of a communication cable. Note that the communication of receiving the X-ray image information may be wired or wireless communication. As a modified example of the X-ray dose management system 1C, a CMOS sensor varying in a manufacturing process and a signal reading method from the CCD sensor may be used instead of the CCD sensor 50C as the X-ray imaging element.

[Operation of X-Ray Dose Management System]

Figure 7:
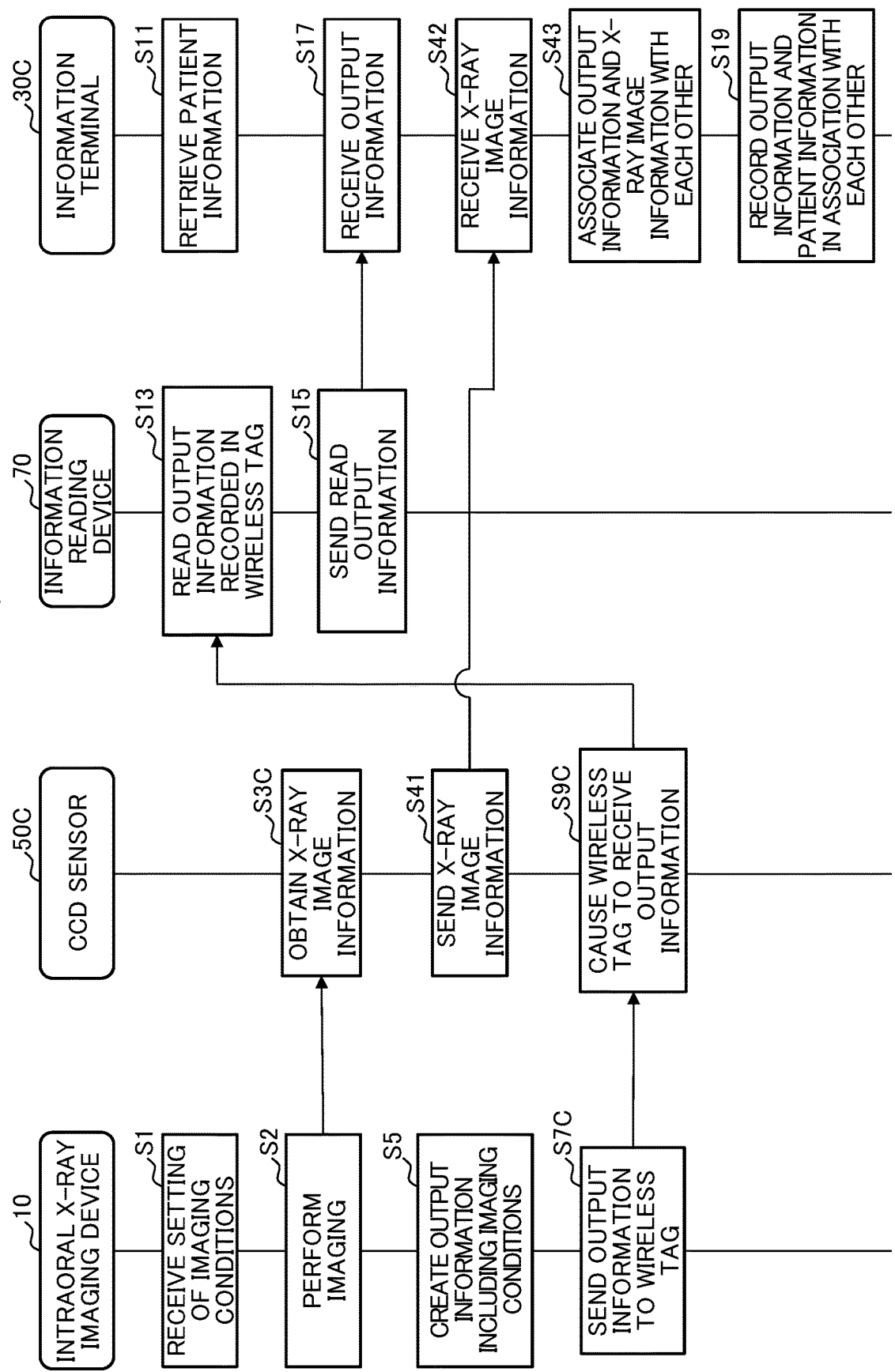
FIG. 7 is a sequence diagram schematically showing a flow of a process in the X-ray dose management system according to the third embodiment of the present invention.

Next, an operation of the X-ray dose management system 1C is described with reference to FIG. 7 (with reference to FIG. 6 as appropriate). Note that, in the following description, the same processes as those in the first embodiment are denoted by the same reference numerals with description thereof omitted as appropriate and different functions and different processes are described.

The intraoral X-ray imaging device 10 receives the setting of the imaging conditions (step S1) and performs imaging (step S2). The CCD sensor 50C obtains the X-ray image information (step S3C) and sends the X-ray image information to the information terminal 30C (step S41). The information terminal 30C receives the X-ray image information from the CCD sensor 50C (step S42). Then, the intraoral X-ray imaging device 10 creates the output information (step S5) and sends the output information to the wireless tag 60 provided in the CCD sensor 50C (step S7C). The wireless tag 60 provided in the CCD sensor 50C receives the output information (step S9C).

Moreover, the operator brings the CCD sensor 50C with the wireless tag 60 close to the information reading device 70. The information reading device 70 reads the output information recorded in the wireless tag 60 (step S13) and sends the read output information to the information terminal 30C (step S15). The information terminal 30C thereby receives the output information from the information reading device 70 (step S17). Then, in the information terminal 30C, the image information processor 35 associates the output information received in step S17 and the X-ray image information received in step S42 with each other (step S43). Moreover, the information terminal 30C records the received output information and the patient information retrieved in step S11 in association with each other (step S19). Note that step S17 and step S42 may be executed in the reverse order.

Figure 3C:
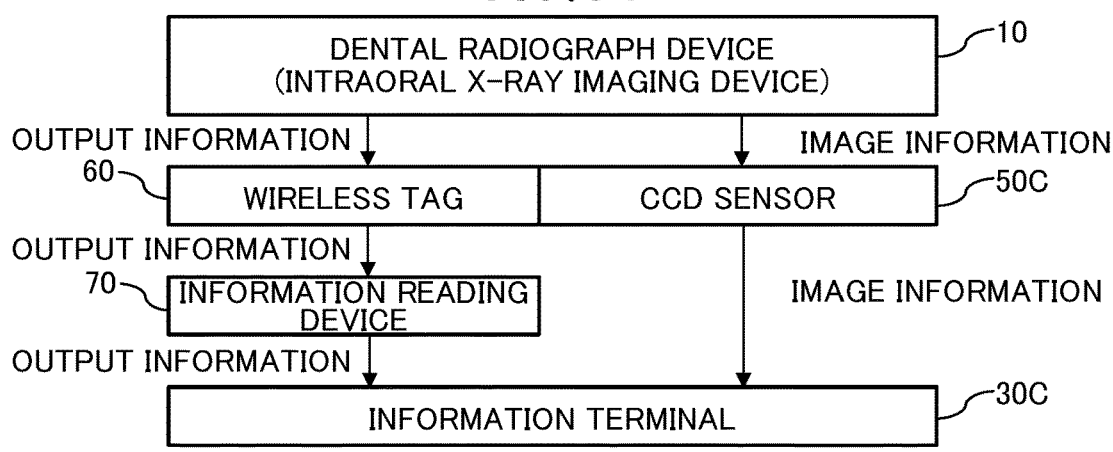
FIG. 3C is a block diagram schematically showing a flow of information in an X-ray dose management system according to a third embodiment of the present invention.

As shown in a left portion of FIG. 3C, the aforementioned output information is transmitted in the order of the dental radiograph device (intraoral X-ray imaging device) 10 to the wireless tag 60, to the information reading device 70, and to the information terminal 30C. The X-ray dose management system 1C can thereby manage the exposed dose of each patient as in the first embodiment. Note that, as shown in a right portion of FIG. 3C, the image information is transmitted in the order of the dental radiograph device (intraoral X-ray imaging device) 10 to the CCD sensor 50C, and to the information terminal 30C.

Fourth Embodiment

Next, description is given of an embodiment capable of handling also the case where the X-ray imaging element 50 includes no wireless tag 60. Note that, in the following description of the embodiment, the same configurations as those in the first embodiment are denoted by the same reference numerals with description thereof omitted as appropriate and different functions and different configurations are described.

[Configuration of X-Ray Dose Management System]

Figure 8:
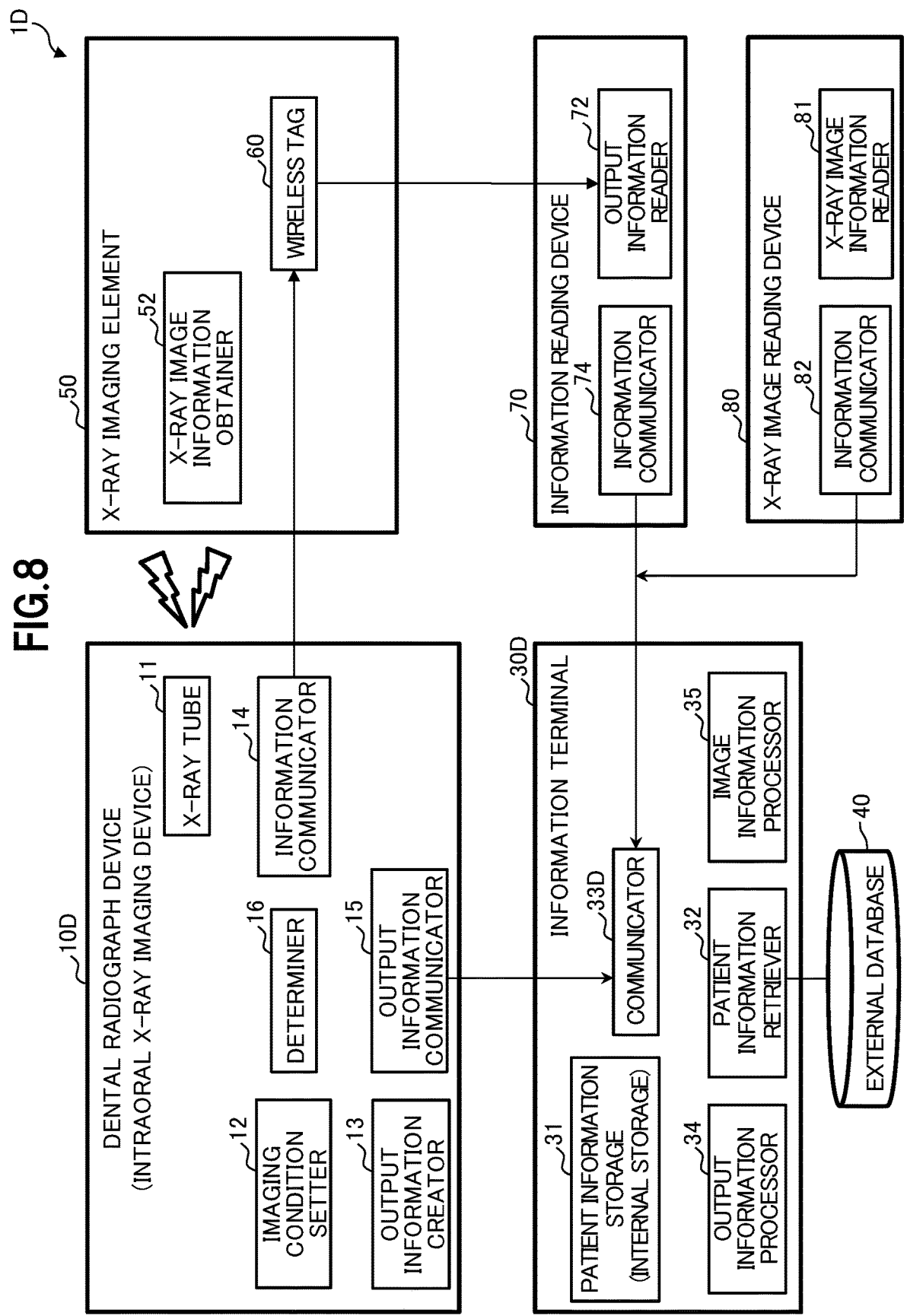
FIG. 8 is a block diagram schematically showing a configuration of an X-ray dose management system according to a fourth embodiment of the present invention.
Figure 10A:
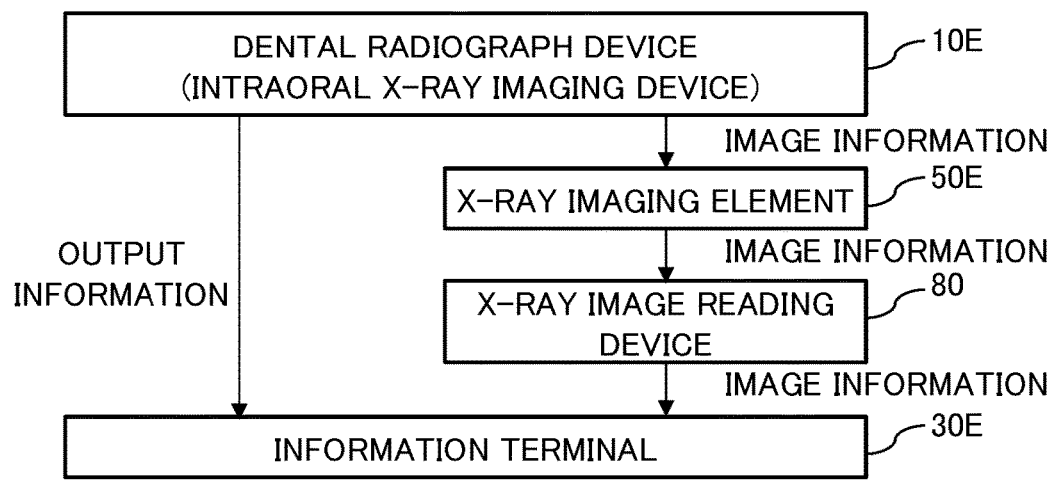
FIG. 10A is a block diagram schematically showing a flow of information in an X-ray dose management system according to a fifth embodiment of the present invention.
Figure 10B:
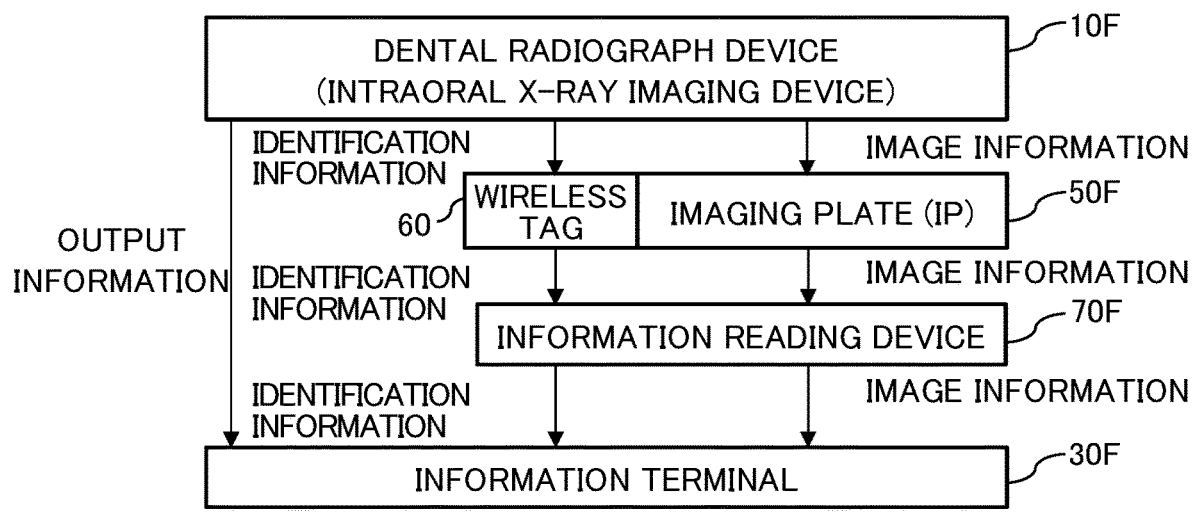
FIG. 10B is a block diagram schematically showing a flow of information in an X-ray dose management system according to a sixth embodiment of the present invention.

As shown in FIG. 8, the X-ray dose management system 1D includes an intraoral X-ray imaging device 10D, the X-ray imaging element 50, the information reading device 70, and an information terminal 30D. The intraoral X-ray imaging device 10D includes the X-ray tube 11, the imaging condition setter 12 that is the controller, the output information creator 13, the information communicator 14, a determiner 16, and an output information communicator 15.

The determiner 16 is a unit that determines whether the X-ray imaging element 50 has the wireless tag 60 or not. Means for detecting presence or absence of the wireless tag 60 is, for example, a sensor or a camera. For example, a sensor that detects presence of an object by using infrared light, ultrasonic wave, visible light, or the like can be used as the sensor. The sensor may be a photoelectric sensor that contactlessly detects presence or absence of an object. The output information communicator 15 sends the output information to the information terminal 30D by wireless communication when the determiner 16 determines that the X-ray imaging element 50 has no wireless tag 60. A wireless communication standard includes, for example, wireless LAN (local area network) such as Wi-Fi (registered trademark), Bluetooth (registered trademark), and ZigBee (registered trademark). Note that, when the X-ray imaging element 50 has the wireless tag 60, the information communicator 14 operates in the same way as in the first embodiment.

The information terminal 30D includes the patient information storage (internal storage) 31, the patient information retriever 32, a communicator 33D, the output information processor 34, and the image information processor 35.

The communicator 33D receives the output information from the output information communicator 15 of the intraoral X-ray imaging device 10D by wireless communication.

[Operation of X-Ray Dose Management System]

Next, an operation of the X-ray dose management system 1D is described with reference to FIG. 9 (with reference to FIG. 8 as appropriate). The sequence diagram of FIG. 9 is the same as the sequence diagram of FIG. 2 except for the processes of steps S6 and S8. Before the sending of the output information to an external device, in the intraoral X-ray imaging device 10D, the determiner 16 determines whether the X-ray imaging element 50 has the wireless tag 60 or not (step S6). When the X-ray imaging element 50 has the wireless tag 60 (step S6: Yes), the intraoral X-ray imaging device 10D sends the output information to the wireless tag 60 (step S7). Meanwhile, when the X-ray imaging element 50 has no wireless tag 60 in step S6 (step S6: No), the output information communicator 15 sends the output information to the information terminal 30D by wireless communication (step S8). Since the processes of the X-ray dose management system 1D hereinafter are the same as those of the X-ray dose management system 1 in the first embodiment, description thereof is omitted.

Although the X-ray dose management system 1D according to the fourth embodiment is described to have the mode in which the output information is transmitted to the information terminal 30D via the wireless tag 60 and the mode in which the output information is transmitted directly to the information terminal 30D, the mode in which the output information is transmitted to the information terminal 30D via the wireless tag 60 is not essential. As embodiments in which the output information is directly transmitted from the intraoral X-ray imaging device 10 to the information terminal 30, X-ray dose management systems 1E, 1F, 1G, and 1H in fifth, sixth, seventh, and eighth embodiments are described below with reference to FIGS. 10 to 18. FIGS. 10A, 10B, 10C, and 10D schematically show outlines and information flows of the X-ray dose management systems 1E, 1F, 1G, and 1H in the fifth, sixth, seventh, and eighth embodiments. The embodiments are described one by one in detail.

Fifth Embodiment

[Configuration of X-Ray Dose Management System]

As shown in FIG. 11, the X-ray dose management system 1E includes an intraoral X-ray imaging device 10E, an X-ray imaging element 50E, and an information terminal 30E. Note that, in the following description of the embodiment, the same configurations as those in the first embodiment are denoted by the same reference numerals with description thereof omitted as appropriate and different functions and different configurations are described. The intraoral X-ray imaging device 10E includes the X-ray tube 11, the imaging condition setter 12 that is the controller, the output information creator 13, and the output information communicator 15. The output information communicator 15 sends the output information to the information terminal 30E that is the external device by wireless communication.

The X-ray imaging element 50E includes the X-ray image information obtainer 52. The information terminal 30E includes the patient information storage (internal storage) 31, the patient information retriever 32, a communicator 33E, and the output information processor 34. The communicator 33E receives the output information from the output information communicator 15 of the intraoral X-ray imaging device 10E by wireless communication.

[Operation of X-Ray Dose Management System]

Next, an operation of the X-ray dose management system 1E is described with reference to FIG. 12 (with reference to FIG. 11 as appropriate). Note that, in the following description, the same processes as those in the first embodiment are denoted by the same reference numerals with description thereof omitted as appropriate and different functions and different processes are described.

The intraoral X-ray imaging device 10E receives the setting of the imaging conditions (step S1) and performs imaging (step S2). The X-ray imaging element 50E obtains the X-ray image information (step S3B). Then, the intraoral X-ray imaging device 10E creates the output information including the identification information of the imaging time and date, the dose information, and imaging conditions (step S5). Next, the intraoral X-ray imaging device 10E sends the output information to the information terminal 30E that is the external device by wireless communication (step S51). The information terminal 30E receives the output information from the intraoral X-ray imaging device 10E by wireless communication (step S52).

Meanwhile, the operator operates the information terminal 30E to retrieve the patient information on the patient subjected to X-ray imaging from the patient information storage 31 or the external database 40 in which the patient information is stored, in the information terminal 30E (step S11). Then, the information terminal 30E records the output information received in step S52 and the patient information retrieved in step S11 in association with each other in the patient information storage 31 or the external database 40 (step S19). The X-ray dose management system 1E can thereby manage the exposed dose of each patient as in the first embodiment.

Moreover, when the X-ray imaging element 50E is, for example, the IP, the X-ray image reading device 80 reads the X-ray image information recorded in the IP (X-ray imaging element 50E) (step S53). Then, the X-ray image reading device 80 sends the read X-ray image information to the information terminal 30E (step S54). The information terminal 30E thereby receives the X-ray image information (step S55). Moreover, in the state where the patient information is retrieved in step S11, the operator can operate the information terminal 30E to manually associate the output information received in step S52 and the X-ray image information received in step S55 with each other (step S56).

Sixth Embodiment

Next, description is given of an embodiment in which the identification information for identifying the imaging time and date is used by being recorded in the wireless tag 60 provided in the X-ray imaging element 50.

[Configuration of X-Ray Dose Management System]

Figure 13:
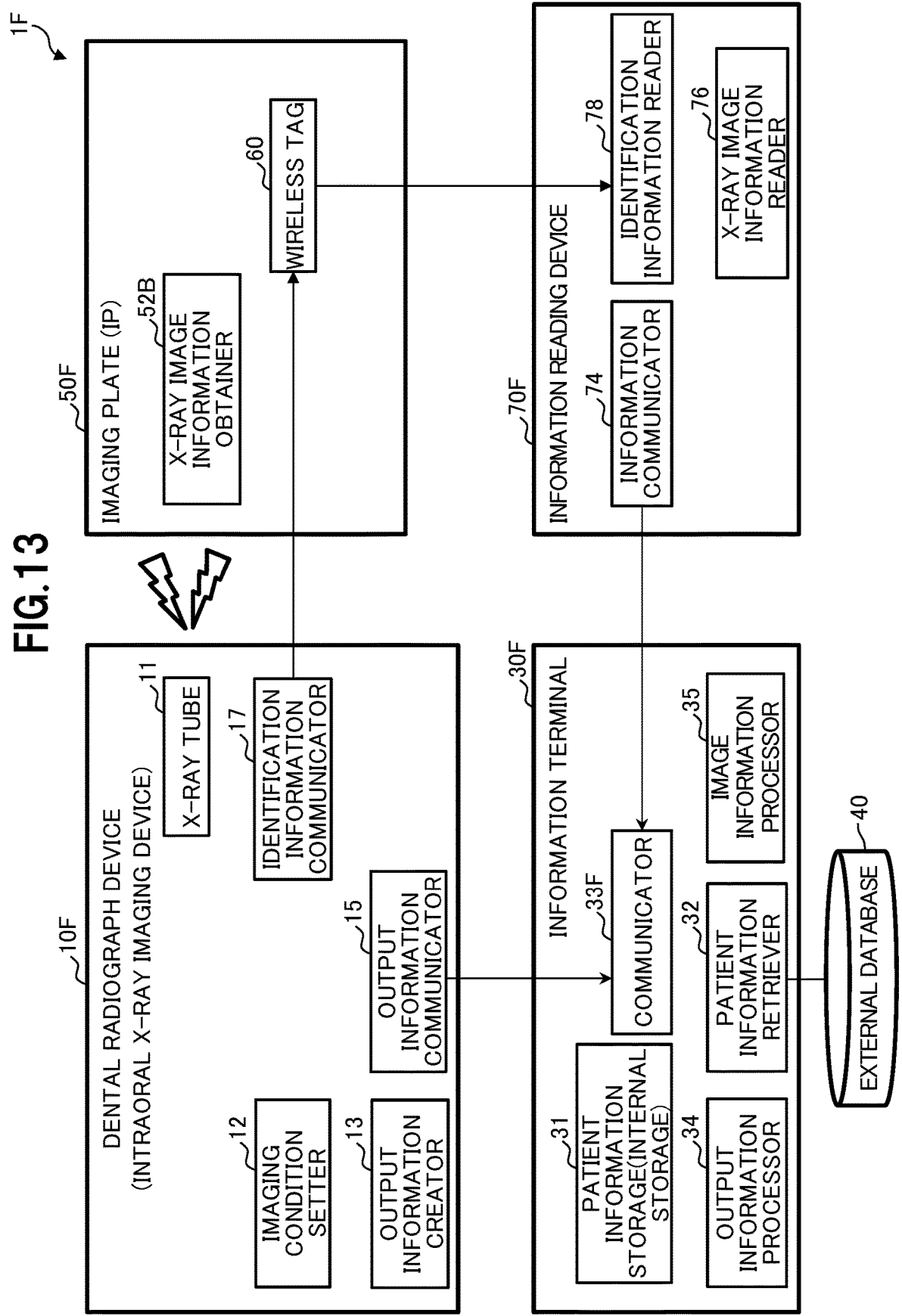
FIG. 13 is a block diagram schematically showing a configuration of the X-ray dose management system according to the sixth embodiment of the present invention.

As shown in FIG. 13, an X-ray dose management system 1F includes an intraoral X-ray imaging device 10F, an IP 50F that is the X-ray imaging element, an information reading device 70F, and an information terminal 30F. Note that, in the following description of the embodiment, the same configurations as those in the first embodiment are denoted by the same reference numerals with description thereof omitted as appropriate and different functions and different configurations are described.

The intraoral X-ray imaging device 10F includes the X-ray tube 11, the imaging condition setter 12 that is the controller, the output information creator 13, the output information communicator 15, and an identification information communicator 17. The identification information communicator 17 is a unit that sends the identification information of the imaging time and date of the X-ray imaging to the wireless tag 60 provided in the IP 50F. When the wireless tag 60 is a tag that uses RFID, the identification information communicator 17 includes a RFID reader-writer. In this case, the identification information of the imaging time and date is information for identifying a captured X-ray image and specifying the output information such as the imaging conditions of the captured X-ray image. The identification information is expressed as, for example, hour, minute, and second of the imaging date. As a modified example, the identification information may be a count value obtained by counting the number of times of imaging or the number of captured images in each imaging date.

The information reading device 70F includes the X-ray image information reader 76, an identification information reader 78, and the information communicator 74. The X-ray image information reader 76 is a unit that reads the X-ray image information recorded in the IP 50F. The identification information reader 78 is a unit that reads the identification information of the imaging time and date recorded in the wireless tag 60. When the wireless tag 60 is a tag that uses RFID, the identification information reader 78 includes a RFID reader-writer. The information communicator 74 sends the read X-ray image information and the read identification information of the imaging time and date to the information terminal 30F. The X-ray image information reader 76 and the information communicator 74 may be formed of a so-called IP scanner. Specifically, the information reading device 70F can be formed by arranging the identification information reader 78 formed of, for example, a RFID reader-writer in a predetermined portion of a publicly known IP scanner.

The information terminal 30F includes the patient information storage (internal storage) 31, the patient information retriever 32, a communicator 33F, the output information processor 34, and the image information processor 35. The communicator 33F receives the output information from the intraoral X-ray imaging device 10F and also receives the X-ray image information and the identification information of the imaging time and date from the information reading device 70F. The image information processor 35 matches the identification information of the imaging time and date received from the information reading device 70F against the identification information of the imaging time and date included in the output information and associates the X-ray image information identified by using the identification information received from the information reading device 70F with the output information.

[Operation of X-Ray Dose Management System]

Figure 14:
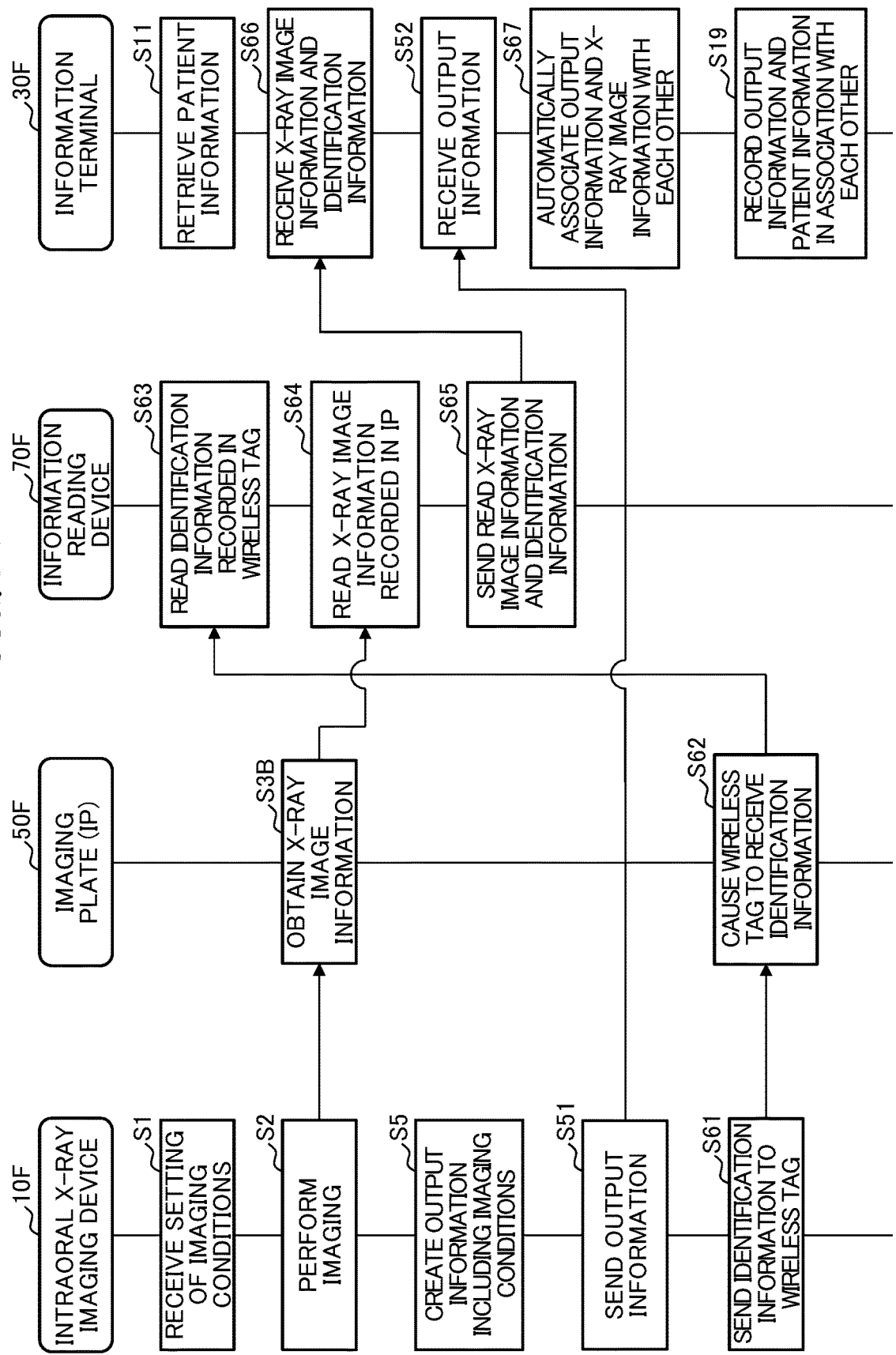
FIG. 14 is a sequence diagram schematically showing a flow of a process in the X-ray dose management system according to the sixth embodiment of the present invention.

Next, an operation of the X-ray dose management system 1F is described with reference to FIG. 14 (with reference to FIG. 13 as appropriate). Note that, in the following description, the same processes as those in the fifth embodiment are denoted by the same reference numerals with description thereof omitted and different functions and different processes are described.

In the intraoral X-ray imaging device 10F, the identification information communicator 17 sends the identification information of the imaging time and date to the wireless tag (step S61). The wireless tag 60 provided in the IP 50F receives the identification information (step S62). Then, in the information reading device 70F, the identification information reader 78 reads the identification information of the imaging time and date (imaging date, hour, minute, second) recorded in the wireless tag 60 (step S63). Moreover, in the information reading device 70F, the X-ray image information reader 76 reads the X-ray image information recorded in the IP 50F (step S64).

Then, in the information reading device 70F, the information communicator 74 sends the read X-ray image information and the read identification information of the imaging time and date to the information terminal 30F (step S65). In the information terminal 30F, the communicator 33F receives the X-ray image information and the identification information from the information reading device 70F (step S66). Then, in the information terminal 30F, the image information processor 35 automatically associates the output information received in step S52 and the X-ray image information received in step S66 with each other based on the identification information of the imaging time and date (step S67). Moreover, the information terminal 30F can record the output information received in step S52 and the patient information retrieved in step S11 in association with each other (step S19).

Normally, it is impossible to find out when the X-ray image information recorded in the X-ray imaging element is imaged only from the X-ray imaging element. However, since the X-ray dose management system 1F records the identification information for identifying the imaging time and date in the wireless tag 60 provided in the IP 50F and uses it, the received X-ray image information and the output information can be automatically associated with each other as a result of the matching in step S67.

Seventh Embodiment

Description is given of an embodiment in which the association of the X-ray image information and the output information is performed on the information reading device side instead of the information terminal side.

[Configuration of X-Ray Dose Management System]

Figure 15:
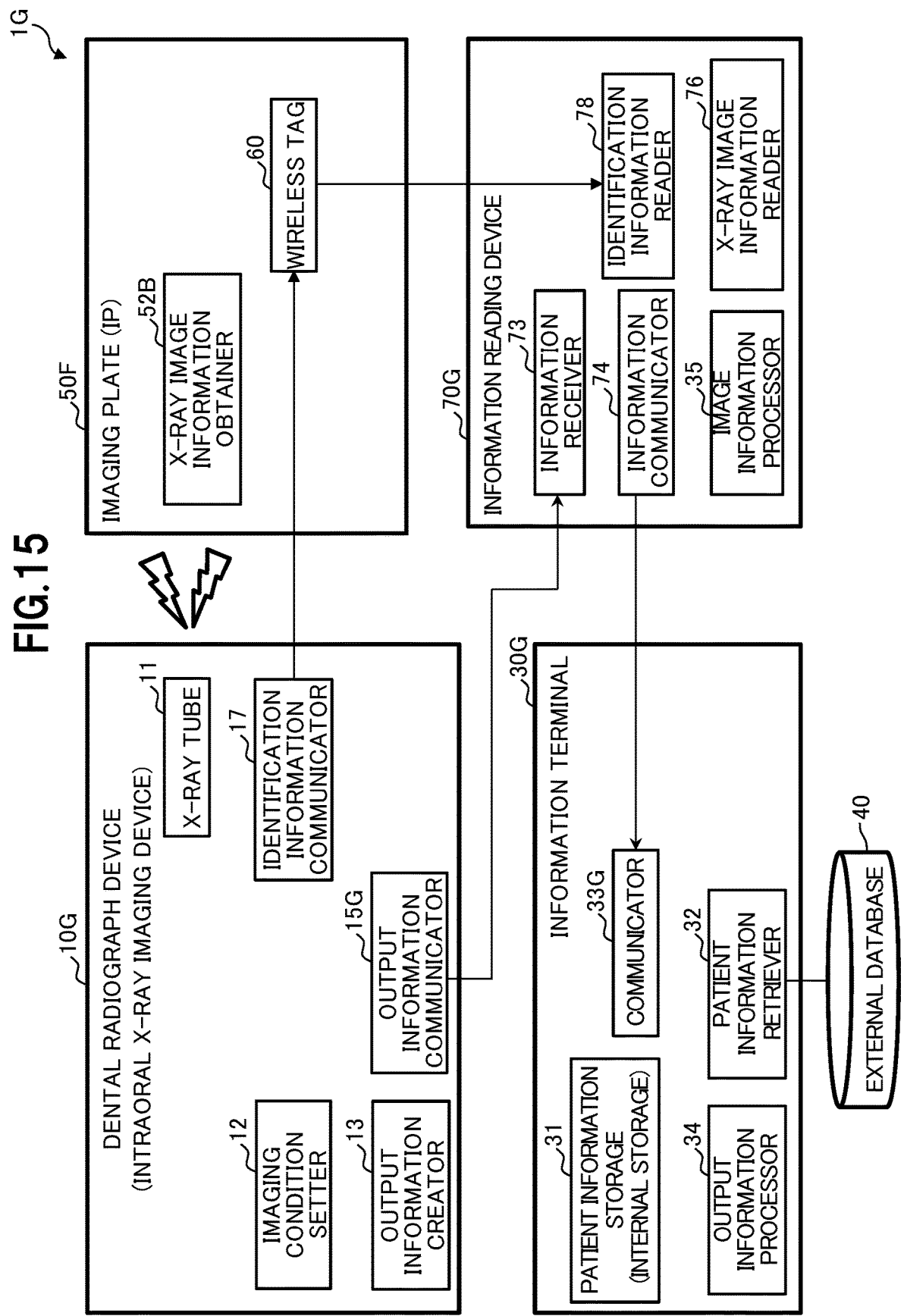
FIG. 15 is a block diagram schematically showing a configuration of the X-ray dose management system according to the seventh embodiment of the present invention.

As shown in FIG. 15, the X-ray dose management system 1G includes an intraoral X-ray imaging device 10G, the IP 50F that is the X-ray imaging element, an information reading device 70G, and an information terminal 30G. Note that, in the following description of the embodiment, the same configurations as those in the sixth embodiment are denoted by the same reference numerals with description thereof omitted as appropriate and different functions and different configurations are described.

As shown in FIG. 15, the intraoral X-ray imaging device 10G includes the X-ray tube 11, the imaging condition setter 12 that is the controller, the output information creator 13, an output information communicator 15G, and the identification information communicator 17. The output information communicator 15G is a unit that sends the output information to the information reading device 70G being the external device by wireless communication. The output information communicator 15G sends the output information to the information reading device 70G by the aforementioned wireless communication.

The information reading device 70G includes the X-ray image information reader 76, the identification information reader 78, an information receiver 73, the image information processor 35, and the information communicator 74. The information receiver 73 receives the output information from the intraoral X-ray imaging device 10G by wireless communication. The image information processor 35 has the same configuration as that included in the information terminal 30F of the sixth embodiment. Specifically, the image information processor 35 matches the identification information of the imaging time and date read from the wireless tag 60 against the identification information of the imaging time and date included in the output information and associates the X-ray image information identified by using the identification information read from the wireless tag 60 with the output information. The information communicator 74 sends the read X-ray image information and the associated output information to the information terminal 30G.

[Operation of X-Ray Dose Management System]

Figure 16:
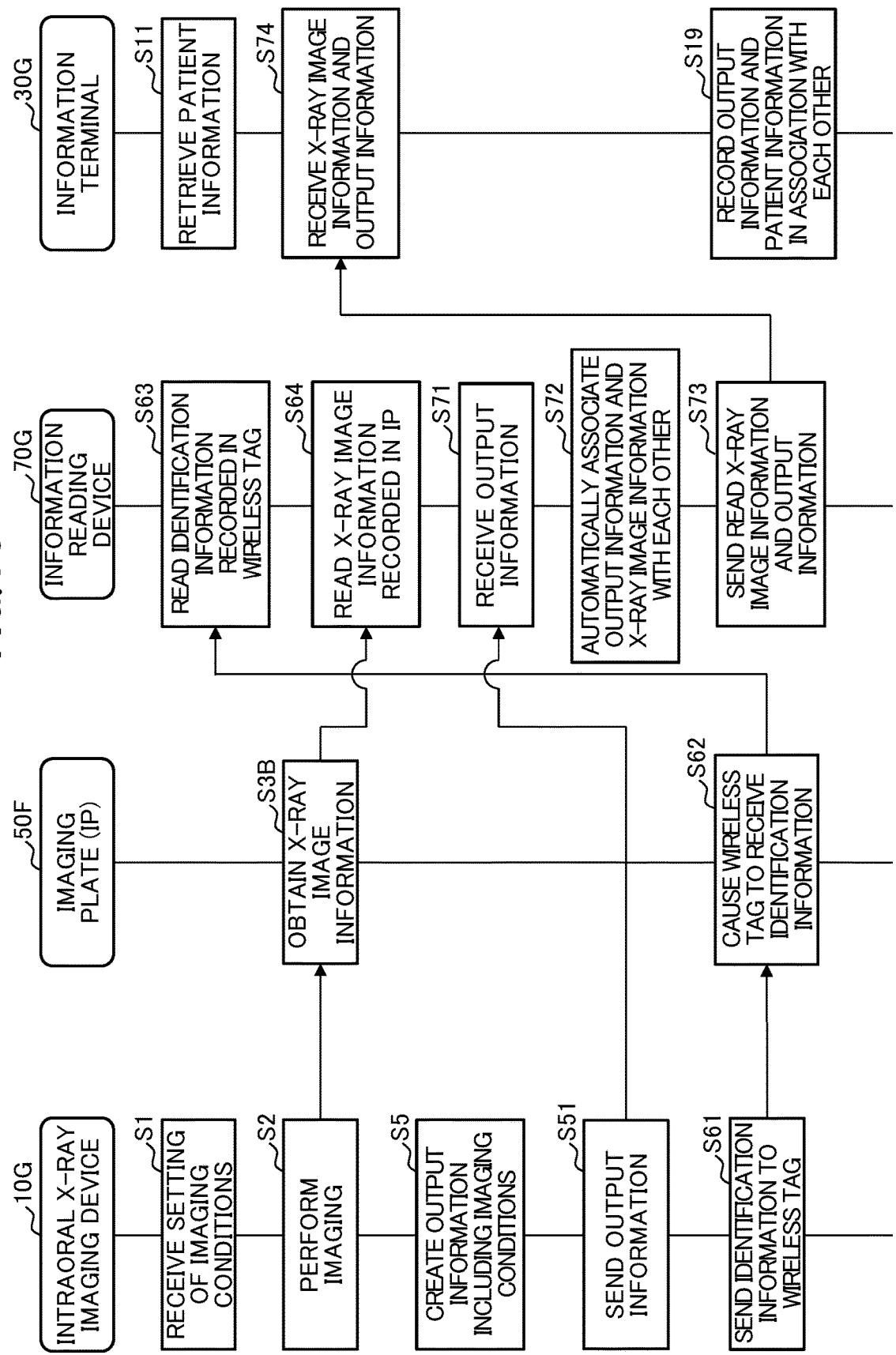
FIG. 16 is a sequence diagram schematically showing a flow of a process in the X-ray dose management system according to the seventh embodiment of the present invention.

Next, an operation of the X-ray dose management system 1G is described with reference to FIG. 16 (with reference to FIG. 15 as appropriate). Note that, in the following description, the same processes as those in the sixth embodiment are denoted by the same reference numerals with description thereof omitted and different functions and different processes are described.

In step S51, the intraoral X-ray imaging device 10G sends the output information to the information reading device 70G that is the external device by wireless communication. In the information reading device 70G, the information receiver 73 receives the output information from the intraoral X-ray imaging device 10G (step S71). Then, in the information reading device 70G, the image information processor 35 automatically associates the output information received in step S71 and the X-ray image information read in step S64 with each other based on the identification information of the imaging time and date (step S72).

Then, the information communicator 74 of the information reading device 70G sends the read X-ray image information and the received output information to the information terminal 30G (step S73). In the information terminal 30G, the communicator 33G receives the X-ray image information and the output information from the information reading device 70G (step S74). The information terminal 30G can thereby record the output information received in step S74 and the patient information retrieved in step S11 in association with each other (step S19).

Eighth Embodiment

Next, description is given of an embodiment in which a CCD sensor is used as the X-ray imaging element and no wireless tag is used.

[Configuration of X-Ray Dose Management System]

Figure 17:
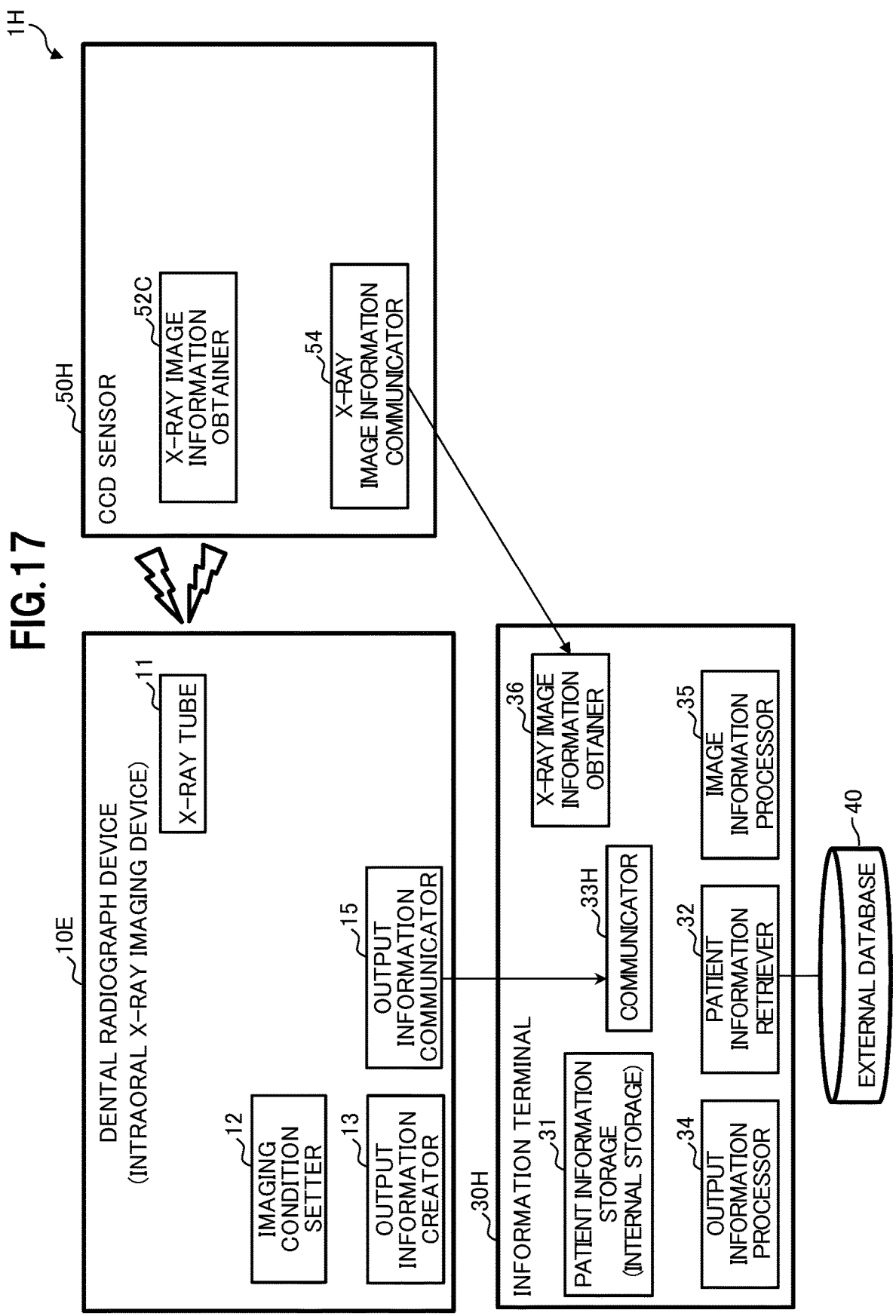
FIG. 17 is a block diagram schematically showing a configuration of the X-ray dose management system according to the eighth embodiment of the present invention.

As shown in FIG. 17, the X-ray dose management system 1H includes the intraoral X-ray imaging device 10E, a CCD sensor 50H that is the X-ray imaging element, and an information terminal 30H. Note that, in the description of the following embodiment, the same configurations as those in the third, fifth, and sixth embodiments are denoted by the same reference numerals with description thereof omitted as appropriate and different functions and different configurations are described.

The CCD sensor 50H includes the X-ray image information obtainer 52C and the X-ray image information communicator 54 and is different from the CCD sensor 50C in the third embodiment in that the CCD sensor 50H includes no wireless tag 60. The information terminal 30H includes the patient information storage (internal storage) 31, the patient information retriever 32, a communicator 33H, the output information processor 34, the X-ray image information obtainer 36, and the image information processor 35. The X-ray image information obtainer 36 obtains the X-ray image information from the CCD sensor 50H. The image information processor 35 associates the output information received by the communicator 33H and the X-ray image information obtained by the X-ray image information obtainer 36 with each other based on the identification information of the imaging time and date included in the output information.

[Operation of X-Ray Dose Management System]

Figure 18:
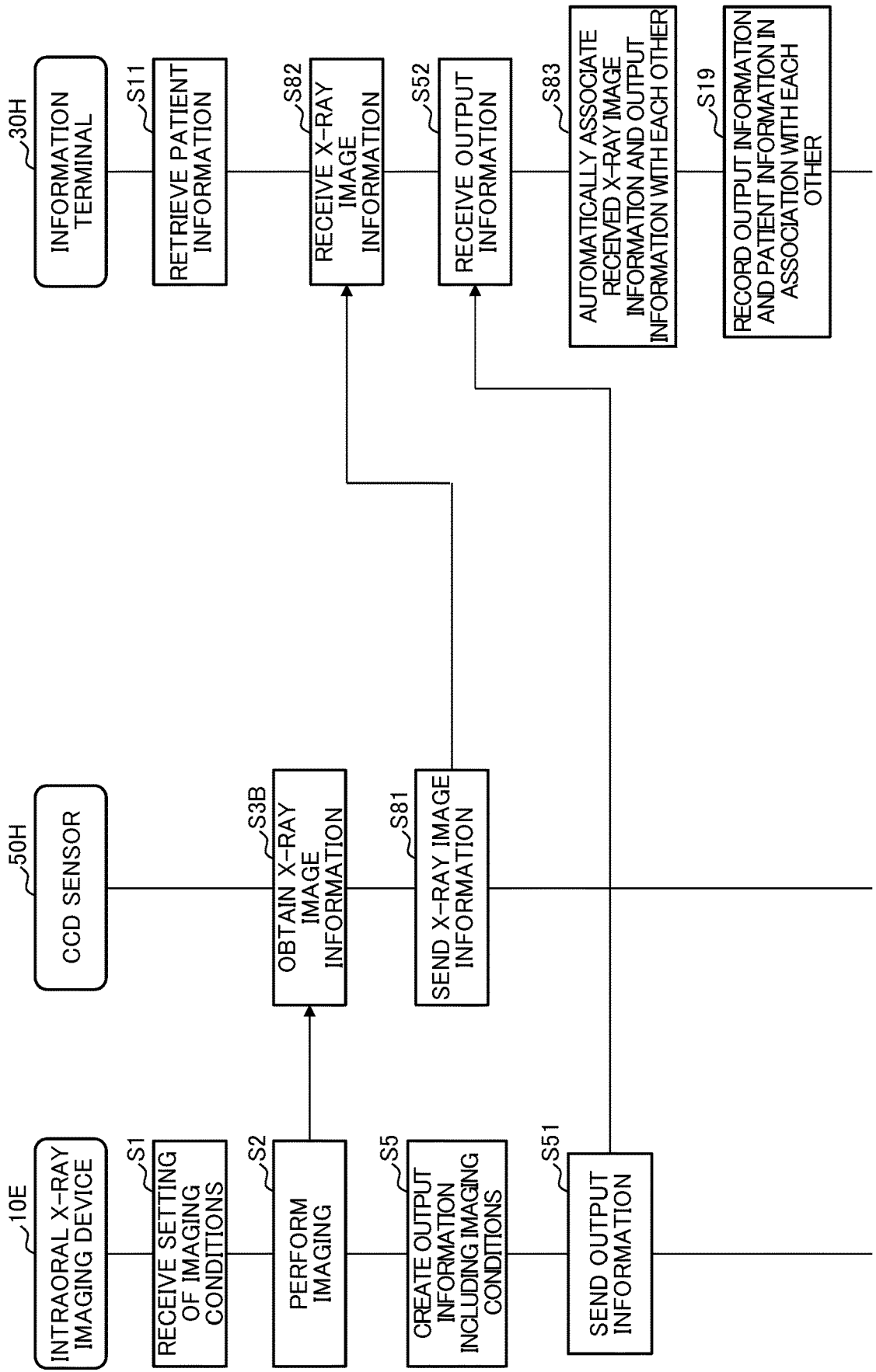
FIG. 18 is a sequence diagram schematically showing a flow of a process in the X-ray dose management system according to the eighth embodiment of the present invention.

Next, an operation of the X-ray dose management system 1H is described with reference to FIG. 18 (with reference to FIG. 17 as appropriate). Note that, in the following description, the same processes as those in the sixth embodiment are denoted by the same reference numerals with description thereof omitted and different functions and different processes are described.

When the CCD sensor 50H that is the X-ray imaging element obtains the X-ray image information acquired by X-ray imaging in step S3B, the CCD sensor 50H sends the obtained X-ray image information to the information terminal 30H (step S81). In the information terminal 30H, the X-ray image information obtainer 36 receives the X-ray image information from the CCD sensor 50H (step S82). Then, in the information terminal 30H, the image information processor 35 automatically associates the output information received in step S52 and the X-ray image information received in step S82 based on the identification information of the imaging time and date (step S83). Moreover, the information terminal 30H can record the output information received in step S52 and the patient information retrieved in step S11 in association with each other (step S19). Note that the X-ray dose management system 1H may use a CMOS sensor instead of the CCD sensor 50H as the X-ray imaging element.

REFERENCE SIGNS LIST 1, 1B, 1C, 1D, 1E, 1F, 1G, 1H X-ray dose management system
10, 10D, 10E, 10F, 10G dental radiograph device (intraoral X-ray imaging device)
11 X-ray tube
12 imaging condition setter
13 output information creator
14 information communicator
15, 15G output information communicator
16 determiner
17 identification information communicator
30 information terminal (external device)
30B, 30C, 30D, 30E, 30F, 30G, 30H information terminal (external device)
31 patient information storage (internal storage)
32 patient information retriever
33, 33B, 33D, 33E, 33F, 33G, 33H communicator
34 output information processor
35 image information processor
36 X-ray image information obtainer
40 external database
50, 50E X-ray imaging element
50B, 50F imaging plate (IP)
50C, 50H CCD sensor
52, 52B, 52C X-ray image information obtainer
54 X-ray image information communicator
60 wireless tag (external device)
70, 70B, 70F, 70G information reading device (external device)
72 output information reader
73 information receiver
74, 74B information communicator
76 X-ray image information reader
78 identification information reader
80 X-ray image reading device
81 X-ray image information reader
82 information communicator

The invention claimed is:
1. An X-ray dose management system comprising:
an intraoral X-ray imaging device;
an X-ray imaging element;
an information reading device; and
an information terminal, wherein
the intraoral X-ray imaging device includes:
an imaging condition setter that is used to set an imaging condition for performing intraoral X-ray imaging;

an output information creator that creates output information including identification information of imaging time and date, dose information, and the imaging condition; and
an information communicator that sends the output information to an external device by wireless communication,
the X-ray imaging element includes:
an X-ray image information obtainer that obtains X-ray image information acquired by X-ray imaging; and
a wireless tag that receives the output information from the intraoral X-ray imaging device,
the information reading device includes:
an output information reader that reads the output information recorded in the wireless tag; and
an information communicator that sends the read output information to the information terminal, and
the information terminal includes:
a patient information retriever that retrieves patient information on a patient subjected to X-ray imaging from an internal storage or an external database in which the patient information is stored;
a communicator that receives the output information; and
an output information processor that records the received output information and the patient information retrieved by the patient information retriever in association with each other in the internal storage or the external database.

2. The X-ray dose management system according to claim 1, wherein
the X-ray imaging element is an imaging plate,
the information reading device includes an X-ray image information reader that reads the X-ray image information recorded in the imaging plate, and
the information communicator sends the read X-ray image information to the information terminal.

3. The X-ray dose management system according to claim 1, wherein
the X-ray imaging element is a CCD sensor or a CMOS sensor,
the X-ray imaging element includes an X-ray image information communicator that sends the X-ray image information to the information terminal, and
the information terminal includes an X-ray image information obtainer that is used to obtain the X-ray image information.

4. The X-ray dose management system according to claim 2, wherein at least one of the information reading device and the information terminal includes an image information processor that associates the output information and the X-ray image information with each other.

5. The X-ray dose management system according to claim 3, wherein the information terminal includes an image information processor that associates the output information and the X-ray image information with each other.

6. The X-ray dose management system according to claim 1, wherein the wireless tag is RFID.

7. The X-ray dose management system according to claim 1, wherein the intraoral X-ray imaging device includes:
a determiner that determines whether the X-ray imaging element has the wireless tag or not, and
an output information communicator that sends the output information to the information terminal by wireless communication when the determiner determines that the X-ray imaging element does not have the wireless tag.

8. An X-ray dose management system comprising:
an intraoral X-ray imaging device;
an X-ray imaging element; and
an information terminal, wherein
the intraoral X-ray imaging device includes:
an imaging condition setter that is used to set an imaging condition for performing intraoral X-ray imaging;
an output information creator that creates output information including identification information of imaging time and date, dose information, and the imaging condition; and
an output information communicator that sends the output information to an external device by wireless communication,
the X-ray imaging element includes an X-ray image information obtainer that obtains X-ray image information acquired by X-ray imaging, and
the information terminal includes:
a patient information retriever that retrieves patient information on a patient subjected to X-ray imaging from an internal storage or an external database in which the patient information is stored;
a communicator that receives the output information; and
an output information processor that records the received output information and the patient information retrieved by the patient information retriever in association with each other in the internal storage or the external database.

9. The X-ray dose management system according to claim 8, wherein
the intraoral X-ray imaging device includes an identification information communicator that sends the identification information of imaging time and date of X-ray imaging to a wireless tag provided in an imaging plate,
the X-ray dose management system further comprises an information reading device,
the information reading device includes:
an X-ray image information reader that reads the X-ray image information recorded in the imaging plate;
an identification information reader that reads the identification information of imaging time and date recorded in the wireless tag; and
an information communicator that sends the read identification information of imaging time and date and the read X-ray image information to the information terminal, and
the information terminal includes an image information processor that matches the identification information of imaging time and date received from the information reading device against the identification information of imaging time and date included in the output information and associates the X-ray image information identified from the identification information received from the information reading device with the output information.

10. The X-ray dose management system according to claim 8, wherein
the intraoral X-ray imaging device includes an identification information communicator that sends the identification information of imaging time and date of X-ray imaging to a wireless tag provided in an imaging plate,
the X-ray dose management system further comprises an information reading device, the information reading device includes:
an X-ray image information reader that reads the X-ray image information recorded in the imaging plate;
an identification information reader that reads the identification information of imaging time and date recorded in the wireless tag;
an information receiver that receives the output information from the intraoral X-ray imaging device;
an image information processor that matches the identification information of imaging time and date read from the wireless tag against the identification information of imaging time and date included in the output information and associates the X-ray image information identified from the identification information read from the wireless tag with the output information; and
an information communicator that sends the read X-ray image information and the associated output information to the information terminal.

11. The X-ray dose management system according to claim 8, wherein
the X-ray imaging element is a CCD sensor or a CMOS sensor,
the X-ray imaging element includes an X-ray image information communicator that sends the X-ray image information to the information terminal, and
the information terminal includes:
an X-ray image information obtainer that is used to obtain the X-ray image information; and
an image information processor that associates the output information received by the communicator and the X-ray image information obtained by the X-ray image information obtainer based on the identification information of imaging time and date included in the output information.

12. The X-ray dose management system according to claim 1, wherein
the output information includes imaged portion information on an imaged portion, and
the information terminal arranges and displays a captured image at a predetermined position based on the imaged portion information.

13. An X-ray dose management method in an X-ray dose management system including an intraoral X-ray imaging device, an X-ray imaging element, an information reading device, and an information terminal, the X-ray dose management method comprising:
causing the intraoral X-ray imaging device to receive setting of an imaging condition for performing intraoral X-ray imaging;
causing the intraoral X-ray imaging device to create output information including identification information of imaging time and date, dose information, and the imaging condition;
causing the intraoral X-ray imaging device to send the output information to an external device by wireless communication;
causing a wireless tag provided in the X-ray imaging element to receive the output information from the intraoral X-ray imaging device;
causing the information reading device to read the output information recorded in the wireless tag;
causing the information reading device to send the read output information to the information terminal;
causing the information terminal to retrieve patient information on a patient subjected to X-ray imaging from an internal storage or an external database in which the patient information is stored;
causing the information terminal to receive the output information; and
causing the information terminal to record the received output information and the retrieved patient information in association with each other in the internal storage or the external database.

14. An X-ray dose management method in an X-ray dose management system including an intraoral X-ray imaging device, an X-ray imaging element, and an information terminal, the X-ray dose management method comprising:
causing the intraoral X-ray imaging device to receive setting of an imaging condition for performing intraoral X-ray imaging;
causing the intraoral X-ray imaging device to create output information including identification information of imaging time and date, dose information, and the imaging condition;
causing the intraoral X-ray imaging device to send the output information to an external device by wireless communication;
causing the X-ray imaging element to obtain X-ray image information acquired by X-ray imaging
causing the information terminal to retrieve patient information on a patient subjected to X-ray imaging from an internal storage or an external database in which the patient information is stored;
causing the information terminal to receive the output information; and
causing the information terminal to record the received output information and the retrieved patient information in association with each other in the internal storage or the external database.

* * * * *